(12) United States Patent
Hohla et al.

(10) Patent No.: US 8,556,885 B2
(45) Date of Patent: Oct. 15, 2013

(54) IRIS RECOGNITION AND TRACKING FOR OPTICAL TREATMENT

(75) Inventors: Kristian Hohla, Vaterstetten (DE); Thomas Neuhann, Munich (DE); Gerhard Youssefi, Landshut (DE); Roland Toennies, Olching (DE)

(73) Assignee: Bausch & Lomb Incorporated, Rochester, NY (US)

( * ) Notice: Subject to any disclaimer, the term of this patent is extended or adjusted under 35 U.S.C. 154(b) by 1857 days.

(21) Appl. No.: 11/595,386

(22) Filed: Nov. 9, 2006

(65) Prior Publication Data

US 2007/0055222 A1    Mar. 8, 2007

Related U.S. Application Data

(62) Division of application No. 10/110,892, filed as application No. PCT/EP00/10373 on Oct. 20, 2000, now Pat. No. 7,146,983.

(51) Int. Cl.
*A61B 18/20* (2006.01)

(52) U.S. Cl.
USPC ..................................... 606/5; 606/4; 606/10

(58) Field of Classification Search
USPC ........ 606/4–6, 10–12; 351/205–212; 128/898
See application file for complete search history.

(56) References Cited

U.S. PATENT DOCUMENTS

| | | |
|---|---|---|
| 4,641,349 A | 2/1987 | Flom et al. |
| 4,848,340 A | 7/1989 | Bille et al. |
| 4,880,017 A | 11/1989 | Soll et al. |
| 4,995,716 A | 2/1991 | Warnicki et al. |
| 5,036,347 A | 7/1991 | Tsunekawa et al. |
| 5,070,883 A | 12/1991 | Kasahara et al. |
| 5,098,426 A | 3/1992 | Sklar et al. |
| 5,159,361 A | 10/1992 | Cambier et al. |
| 5,214,455 A | 5/1993 | Penney et al. |
| 5,291,560 A | 3/1994 | Daugman |
| 5,293,871 A | 3/1994 | Reinstein et al. |
| 5,512,965 A | 4/1996 | Snook |
| 5,512,966 A | 4/1996 | Snook |
| 5,572,596 A | 11/1996 | Wildes et al. |

(Continued)

FOREIGN PATENT DOCUMENTS

| | | |
|---|---|---|
| EP | 0456166 | 10/1995 |
| EP | 0770370 | 5/1997 |

(Continued)

OTHER PUBLICATIONS

Decision (dated Jan. 19, 2012) of the Technical Board of Appeal relating to the Appeal (filed by proprietor on Jun. 16, 2010.

(Continued)

*Primary Examiner* — Ahmed Farah

(57) ABSTRACT

A system and method are provided in which an iris or eye image is taken during a refractive diagnostic analysis. The image is employed for aligning data from the analysis with data from other refractive analysis instruments, as well as aligning a refractive surgical tool, such as a laser, with the eye for treatment. Further, the stored iris image is compared with the patient's iris before treatment, verifying that the correct eye is to be treated with a developed treatment pattern. A variety of refractive instruments can be used, such as corneal topography systems and wavefront aberration systems.

15 Claims, 15 Drawing Sheets

(56) References Cited

U.S. PATENT DOCUMENTS

| | | | |
|---|---|---|---|
| 5,620,436 | A | 4/1997 | Lang et al. |
| 5,685,832 | A | 11/1997 | Chen |
| 5,740,803 | A | 4/1998 | Gray et al. |
| 5,777,719 | A * | 7/1998 | Williams et al. .............. 351/212 |
| 5,865,832 | A | 2/1999 | Knopp et al. |
| 5,891,132 | A | 4/1999 | Hohla |
| 5,923,399 | A | 7/1999 | Van de Velde |
| 5,980,513 | A | 11/1999 | Frey et al. |
| 6,079,828 | A | 6/2000 | Fujieda |
| 6,419,671 | B1 | 7/2002 | Lemberg |
| 6,702,806 | B2 | 3/2004 | Gray et al. |
| 6,793,654 | B2 | 9/2004 | Lemberg |
| 6,913,603 | B2 * | 7/2005 | Knopp et al. ................... 606/10 |

FOREIGN PATENT DOCUMENTS

| | | |
|---|---|---|
| EP | 0765648 | 1/2004 |
| EP | 1153570 | 7/2004 |
| EP | 1210003 | 8/2004 |
| EP | 1280484 | 6/2007 |
| EP | 1514509 | 3/2009 |
| EP | 1221890 | 6/2009 |
| WO | 9201417 | 2/1992 |
| WO | 9316631 | 9/1993 |
| WO | 9418883 | 9/1994 |
| WO | 9527453 | 10/1995 |
| WO | 9611655 | 4/1996 |
| WO | 9746183 | 12/1997 |
| WO | 9927334 | 6/1999 |
| WO | 0027273 | 5/2000 |
| WO | 0111418 | 2/2001 |
| WO | 0166029 | 9/2001 |
| WO | 0178584 | 10/2001 |
| WO | 0185045 | 11/2001 |
| WO | 0185075 | 11/2001 |
| WO | 0287442 | 11/2002 |

OTHER PUBLICATIONS

Appeal (filed by proprietor on Aug. 18, 2010) regarding the Decision of Apr. 8, 2010.

Decision (Apr. 8, 2010) regarding Opposition 1 (Jun. 26, 2007) and Opposition 2 (Jun. 27, 2007).

Opposition 1 (Sensomotoric Instruments GmbH) dated Jun. 26, 2007.

Opposition 2 (Visx Incorporated a/k/a AMO Manufacturing) dated Jun. 27, 2007.

Chiron Vision Technolas, Keracor Laser Excimer User Manual, Version 1.0, Aug. 7, 1996.

Sensomotoric Instruments GmbH, VOG for Windows User Manual for Three-Dimensional Video-Oculography Eye Movement Analysis System, Version 3.08, Nov. 1996.

Markham, et al, "Eye Torsion in Space and During Static Tilt Pre-and Post-Spaceflight," Proceedings Sixth European Symposium on Life Sciences Research in Space, Trondheim, Norway, Jun. 16-20, 1996, ESA SP-360 (Oct. 1996).

Bos, et al, "Ocular Torsion Quantification with Video Images," IEEE Transactions on Biomedical Engineering, vol. 41, No. 4, Apr. 1994.

Koch, Douglas, Consultation Section of the J Cataract Refract Surg. vol. 24, Jul. 1998, pp. 876-881.

Suzuki A. Maedna N., et al "Using a reference point and videokeratography for inoperative identification of astigmatism axis," J Cataract Refract Surg 1997, vol. 23; 1491-1495.

Liang et al., "Objective measurement of wave aberrations of the human eye with the use of a Hartmann-Shack wave-front sensor," Journal of the Optical Society of America, vol. 11, No. 7, Jul. 1994, pp. 1949-1957.

Liang, et al, "Aberrations and retinal image quality of the normal human eye," Journal of the Optical Society of America, vol. 14, No. 11, Nov. 1997, pp. 2873-2883.

Kremer, Frederik B., "How to keep Your Lasik on Axis," Review of Ophthalmology, Mar. 1999, and www.revophth.com/1999/March__Articles/RPC9Q&A.html.

Yamanobe et al. "Eye Movement Analysis System using Computerized Image Recognition" Arch Otolaiyngol Head Neck Surg. vol. 116, Mar. 1990, pp. 338-341.

Uozata et al, "Centering Surgical Procedures," American Journal of Ophthalmology vol. 103, Mar. 1987, pp. 264-275.

Autonomous Technologies Corporation, T-PRK Operation Manual for Tracker-Assited Photorefractive Keratectomy System, Sep. 2, 1997, vol. IV, Sec. 1, pp. 27 and 43-48.

Groen et al, "Determination of ocular torsion by means of automatic pattern recognition," IEEE Trans Biomed. Eng. May 1996, 43(5):471-9.

Leventon, Michael Emmanuel, "A Registration, Tracking and Visualization System for Image-Guided Surgery," Master-Thesis, Massachusetts Institute of Technology, May 1997.

Chernyak, Dimitri A., "Iris-Based Cyclotorsional Image Alignment Method for Wavefront Registration," IEEE Transactions on Biomedical Engineering vol. 52, No. 12, Dec. 2005, pp. 2032-2040.

Suzuki contribution to Consultation Section of Journal of Cataract Refractive Surgery, vol. 24, Jul. 1998, pp. 876-881.

Minutes of the Oral Proceeding (held on Jan. 19, 2012).

* cited by examiner

US 8,556,885 B2

IRIS RECOGNITION AND TRACKING FOR OPTICAL TREATMENT

CROSS REFERENCE

This application is a divisional of Ser. No. 10/110,892 filed Feb. 20, 2003, filed under 35 USC 371 from International Application PCT/EP00/10373 filed Oct. 20, 2000, and claiming priority from German Application 19950791.0 filed Oct. 21, 1999, German Application 19950790.2 filed Oct. 21, 1999, and German Application 10014479.9 filed Mar. 23, 2000.

TECHNICAL FIELD

The invention relates to systems for ophthalmic refractive surgery, and more particularly to the use of iris recognition and location systems to align refractive diagnostic tools and refractive laser systems with the eye.

BACKGROUND ART

The field of ophthalmology for the past number of years has seen great strides in the development of refractive treatments intended to correct the vision of the eye. These techniques have evolved from the earlier radial keratotomy technique, in which slits in the cornea allowed the cornea to relax and reshape, to present techniques including photorefractive keratectomy ("PRK"), anterior lamellar keratectomy ("ALK"), laser in situ keratomileusis ("LASIK"), and thermal techniques such as laser thermal keratoplasty ("LTK"). All of these techniques strive to provide a relatively quick but lasting correction of vision.

With the development and refinements of these techniques, greater precision has become possible in refractive error correction. In early types of treatments, the precision of the correction was relatively coarse. To provide correction to within plus or minus one diopter of the desired correction for myopia, for example, would be considered an excellent outcome. The types of treatments have become progressively refined, however, allowing more subtle defects to be corrected. Myopia and hyperopia can now be corrected to a high degree of precision with current techniques, and using excimer lasers, higher order effects can also be corrected, such as asphericity and irregular astigmatism.

At the same time, the diagnostic tools to determine what correction is needed have also advanced. Employing topography systems, vision defects can be determined and corrected irrespective of their "regularity". Such techniques are described in U.S. Pat. No. 5,891,132, entitled "Distributed Excimer Laser Surgery System," issued Apr. 6, 1999. A variety of new topography systems, pachymetry systems, wavefront sensors, and overall refractive error detection systems can detect not only the amounts of myopia, hyperopia, and astigmatism, but also, higher order aberrations of the refractive properties of the eye.

Detection of wavefront aberrations in the human eye for such purposes as intraocular surgery and contact lens and intraocular lens fabrication is disclosed, e.g., in Liang et al, "Objective measurement of wave aberrations of the human eye with the user of a Hartmann-Shack wave-front sensor," Journal of the Optical Society of America, Vol. 11, No. 7, July, 1994, pp. 1-9. Improvements to the technique of Liang et al are taught in J. Liang and D. R. Williams, "Aberrations and retinal image quality of the normal human eye," *Journal of the Optical Society of America*, Vol. 4, No. 11, November, 1997, pp. 2873-2883 and in U.S. Pat. No. 5,777,719 to Williams et al. ("Williams"). Williams teaches techniques for detecting aberrations and for using the aberrations thus detected for eye surgery and the fabrication of intraocular and contact lenses.

International Pat. Publication WO 99/27334 (International App. PCT/US97/21688)("Frey") teaches a further variation using polarizing optics to control back-scatter from the lenses in the detector setup. Like Williams, Frey suggests using data from the wavefront sensor to develop an optical correction for the eye examined. More specifically, the optical correction so determined is limited to the aperture of the cornea measured by the sensor, e.g., the 6 millimeter circle to which the eye's pupil was dilated when the eye was measured. Outside that area, Frey suggests using a tapering blend zone of partial ablation to minimize severe changes in corneal curvature and hence lessen regression.

These diagnostic systems and techniques have the potential for permitting correction of both the fundamental and higher order effects, especially when used with the even more refined refractive correction techniques, with the possibility that vision correction to better than 20/20 will someday be the norm. However, improved techniques for applying advancing diagnostic technology to refractive surgery are needed.

SUMMARY OF THE INVENTION

While ophthalmic refractive surgery techniques and ophthalmic refractive diagnostic techniques have become more precise, that precision has lead to an increased need for accuracy. According to the invention, advances in the precision of both the surgical and diagnostic techniques are further realized by using an image of the iris (or a portion of the iris or other identifying eye features) for adjustment during diagnosis and during surgery. Before the refractive procedure is performed, the surgical system is aligned based on an iris image stored during the diagnosis.

For example, according to the invention, a corneal surface topography system or wavefront sensor system acquires refractive characteristic data of the eye, but also acquires a corresponding image of the pupil and iris of the eye. Data corresponding to the iris image is then maintained in connection with data from the diagnostic system. If additional diagnostic tools are employed, they too can employ a pupil or iris imaging camera to provide a "point of normalization" to which all the data and a subsequent treatment are referenced.

When it comes time to perform the refractive treatment, such as using LASIK with an excimer laser, another camera takes an image of the iris, and a treatment developed from the diagnostic information is normalized to that iris image. This normalization can include translation, rotation, scaling, or other transformational techniques. The treatment is then provided with the knowledge that it is being applied to the desired points on the cornea.

Further, the iris image can be provided to an eye tracking system, such that the actual aim of the excimer laser can be adjusted on a dynamic basis relative to the position of the iris.

Preferably, the iris system detects distinctive features in the iris and determines translational functions based on those features. Generally, no two irises are alike, and rotation, translation, scaling, or other transformational techniques can be accomplished based upon the distinctive features. The iris system can store a variety of features of the iris, including an image of the iris itself, as well as derived characteristic features of the iris, features of the pupil and other parts of the eye, or other features that can help to align subsequent data or align the surgical system before laser treatment.

According to different features of the invention, the iris alignment can be performed between diagnostic tools, between a diagnostic tool and a refractive tool such as a laser, or combinations of such tools. Additionally, different alignment techniques can be used between different tools. For example, the iris data can be used to align one diagnostic tool such as a topographic tool with a refractive tool such as a laser, while the outline of the iris and a rotational reference is used to align data between the topography tool and, for example, a wavefront sensor. Other alternatives are possible. In these various techniques, the alignment data is maintained together with the refractive analysis data, or the refractive treatment data, for subsequent use by other refractive analysis or treatment tools.

In summary, the term "diagnostic tools" as used herein, refers to diagnostic devices or systems such as topographers, pachymeters, wavefront sensors, and the like used to make diagnostic measurements to obtain refractive data about the eye being measured. Refractive data thus refers generally to features or characteristics of the eye that cause less than perfect vision including eye component shape, thickness, light propagation and wavefront aberration and other refractive anomalies recognized by those skilled in the art. Likewise, the term "refractive tool" generally refers to a device or system that can perform a refractive treatment on the eye, such as, e.g., an excimer laser which is typically used for photoablation in PRK, LASIK and other photo refractive surgery. The term "normalization" as used herein will be understood from the description to follow to generally mean matching, equating, correlating, fitting, etc., an image or representation of a diagnostic measurement to the first iris image such that everything is size consistent to the first iris image reference coordinate frame.

As an additional benefit, the iris data stored in conjunction with the refractive diagnostic analysis can provide a safety mechanism for subsequent treatment. Specifically, if before surgery the iris data does not match the actual iris image acquired by the surgical system, the surgery can be stopped or prevented. This can prevent an operation on the wrong eye with particular data, for example, or the use of data from another patient.

MODE(S) OF CARRYING OUT THE INVENTION

Use of Iris Data to Align Laser Treatment

Figure 1:
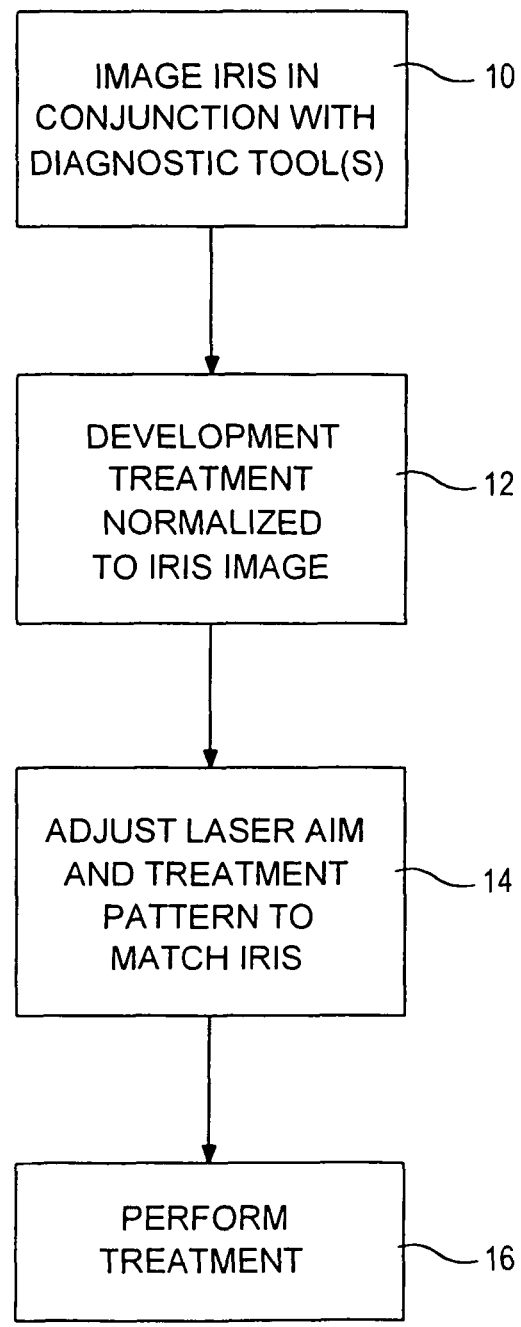
FIG. 1 is a flow diagram illustrating the acquisition of iris image data and the use of the data for a subsequent laser treatment.

FIG. 1 shows the general flow of a method of using a system implemented according to an embodiment of the invention. At block 10, the iris is imaged in conjunction with acquiring refractive data using a diagnostic tool. This imaging and the use of the diagnostic tool can take many forms. For example, the tool can be used well in advance of the laser treatment, such as using a corneal surface topography system to determine a corneal or refractive profile. Or it can be used immediately before refractive surgery. In any case, the imaged iris or some representation of the iris is maintained with the data developed by the diagnostic tool.

Proceeding to block 12, a treatment is then developed based on the data provided by the diagnostic tool. For example, this treatment may treat for a certain degree of myopia and an irregular astigmatism. This treatment can be, for example, a treatment developed using the algorithms of PCT/EP95/04028, entitled "Excimer Laser System for Correction of Vision with Reduced Thermal Effects," published Apr. 25, 1996, which provides a dithering algorithm to modify a corneal profile, in conjunction with the distributed system of U.S. Pat. No. 5,891,132, entitled "Distributed Excimer Laser Surgery System," issued Apr. 6, 1999. This treatment, however, is normalized to the stored representation of the iris image. By doing so, subsequent modifications to the treatment based on additional diagnostic tool data can be normalized to subsequent iris images.

Further, the treatment itself is preferably aligned to the iris of the patient. This is done at block 14, where the laser aim and the treatment pattern are normalized to the image of an iris of the patient under treatment. This normalization can take very general forms, such as a translation of the aim of the laser to an appropriate point, or more sophisticated forms, such as by rotation or even scaling and skewing of the treatment to match the iris image that is presented to the laser system.

Proceeding to block 16, the laser treatment is then performed. Of note, during the laser treatment the system can periodically or even continuously match the iris data to the stored representation of the iris data, in essence tracking the patient's eye.

Figure 2A:
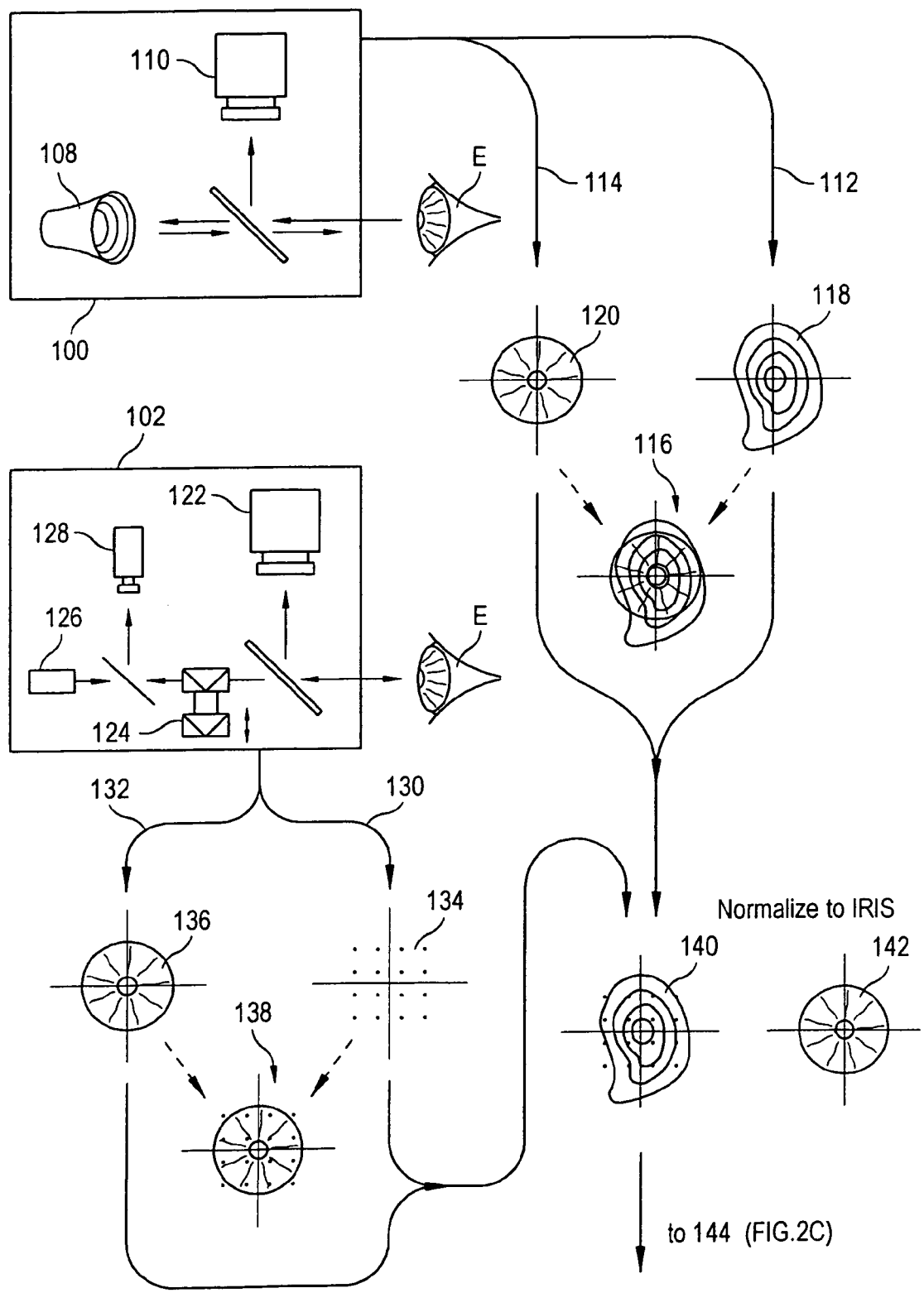
FIGS. 2A, 2B, and 2C are block flow diagrams illustrating the acquisition of iris data in conjunction with refractive characteristic data, the generation of a treatment based on that data, and the use of that treatment data in conjunction with an iris image to perform laser surgery.
Figure 2B:
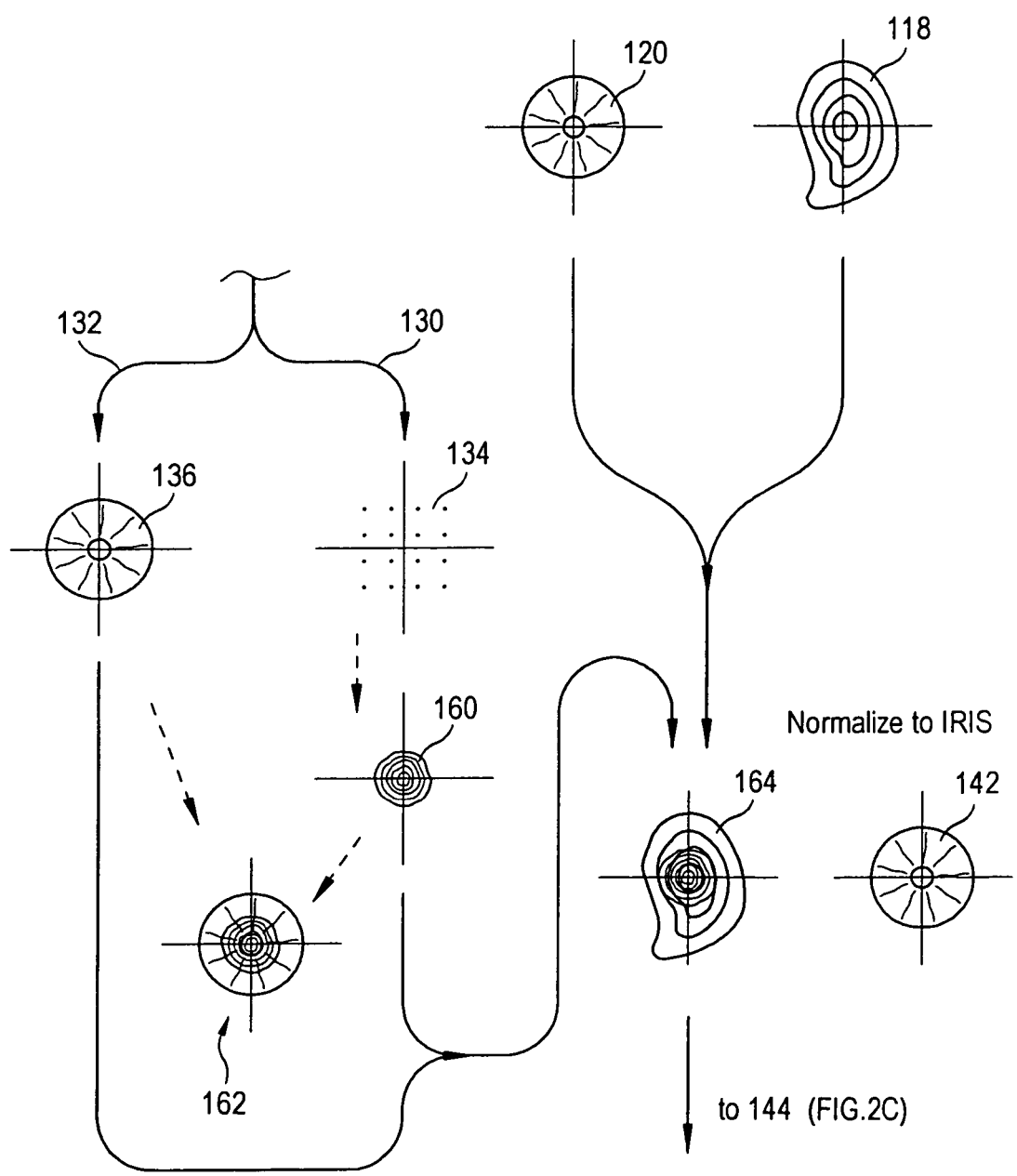
Figure 2C:
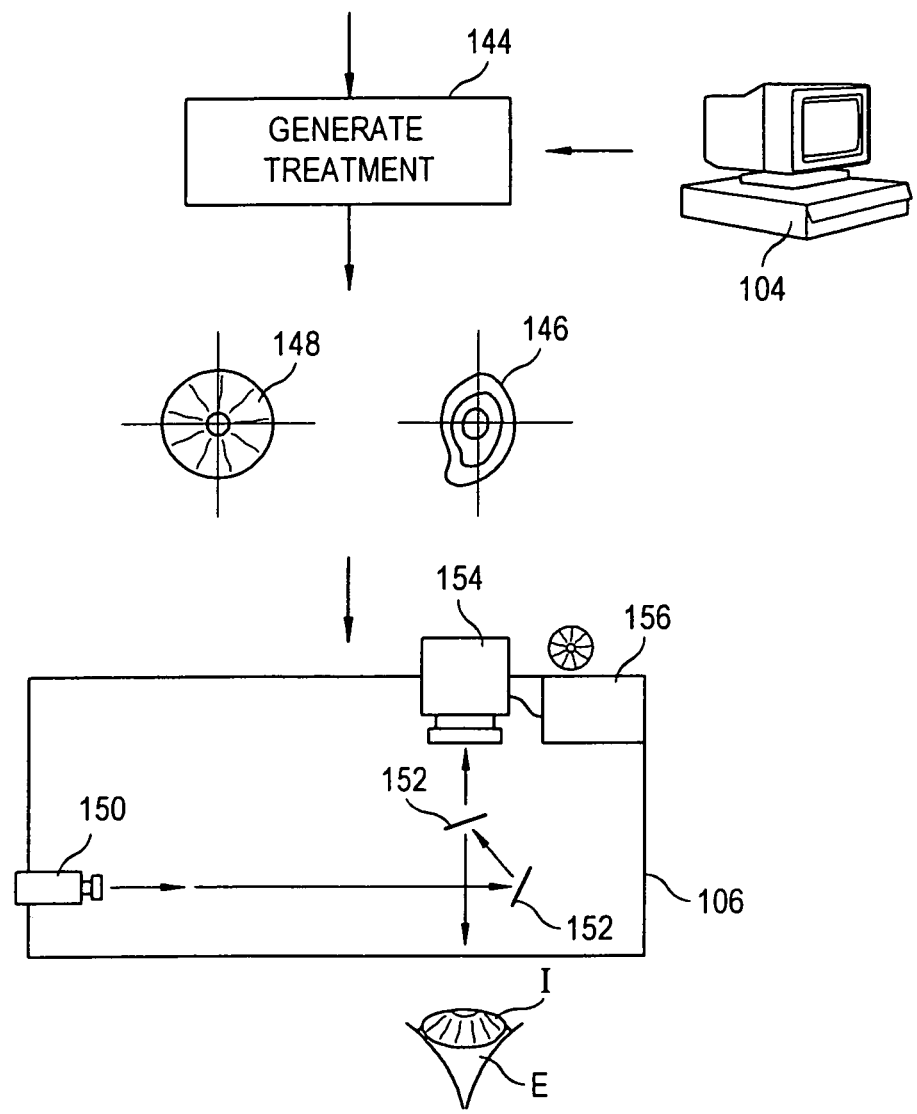

Turning to FIGS. 2A, 2B, and 2C, the general flow of determining refractive data, normalizing to the iris image, generating a course of treatment, and then applying a course of treatment is shown in a system according to the invention. Refractive characteristics of an eye to be treated are determined by a corneal surface topography system 100 and a wavefront sensor 102. Both of these devices generally provide data indicative of refractive characteristics of the eye. In addition, a computer workstation or computational unit 104 is shown that is used to create a customized course of treatment based on the data provided by the diagnostic tool. Although shown as a separate workstation 104, such as for use in a distributed system like that disclosed in PCT/EP97/02821, the workstation 104 and/or its functionality could be incorporated within many of the other components of the system of FIGS. 2A, 2B, and 2C. For example, also shown in FIG. 2C is a laser system 106, which receives both the treatment generated by the workstation 104 and corresponding iris data. The laser system 106 could incorporate the functionality of the workstation 104, generating an appropriate laser treatment within the laser system 106 itself.

Beginning in FIG. 2A, the corneal topography system 100 gathers corneal topographic data from a patient's eye E. The illustrated topography system includes Placido disk-type hardware 108 as well as a pupil or iris camera 110. These components are known to the art, and a variety of techniques are known to produce corneal topographic data. For example, the System 2000 by EyeSys produces corneal topographic data, and ORBSCAN II® topography system by Bausch & Lomb/Orbtek, Inc. of Salt Lake City, Utah, produces not only surface corneal topography, but also overall topography for the various components of the eye. The former system is a Placido disk based system; the latter is an automated slit lamp system. The ORBSCAN II® system uses surface elevations and ray tracing to determine refractive errors of the eye. The topographic system 100 typically can produce data output 112 in a variety of formats and gathered using a variety of techniques, such as absolute corneal height at a variety of points, corneal curvature at a variety of points, and the like.

Besides the corneal data 112, the corneal topography system 100 also acquires a corresponding "snapshot" of the visible surface of the eye E, providing first iris (and pupil) image data 114 representative of an iris (and pupil) image 120. Many corneal surface topography systems have a camera that can acquire this image. As is further discussed below, the camera 110 can provide the iris image data 114 in a variety of formats, such as a standard image format, or as a reduced format in which various iris or pupil artifacts are identified. Such artifacts can include those identifiable along the edge of the interface of the pupil and iris. The iris data 114 can be some combination of image and recognized artifacts of the iris, the pupil, their interface, or other eye structures as well.

The camera 110 can be a variety of camera types, such as a visible light, infrared, or other camera suitable to capture the iris image 120. Preferably, the image is acquired at the same time that the topography components (Placido disk-type hardware) 108 are gathering the topography data 112, although before or after would also be acceptable.

As illustrated in FIG. 2A, the topography data 112 and the iris image data 114 are preferably related according to some coordinate system, as represented by overlaid images 116. The relationship between a determined topography 118 and the iris image 120 is maintained in the data.

As discussed below, the iris image data 114 for the iris image 120 is useful for aligning a surgical tool (here, the laser system 106). The data 114, however, is also useful for normalizing data from various other ophthalmic diagnostic instruments. Specifically, the wavefront sensor 102 also analyzes the refractive irregularities or aberrations in the eye E. In the wavefront sensor 102, preferably a camera 122 is focused onto the eye E in front of certain "trombone" optics 124. The trombone optics 124 (e.g., a focus or optical path adjusting tuning device or optics) is used to change the optical path length and focus a laser 126 onto the retina of the eye E. The trombone optics 124 can be used to determine and compensate for the low order aberrations of the eye E, such as defocus. In one embodiment, the wavefront sensor 102 gathers data for determining optical aberrations in the eye E via a lenslet camera 128. As discussed above, a variety of other wavefront sensors or other type of systems for determining refractive ophthalmic wavefront aberrations can be employed.

As with the corneal surface topography system 100, the wavefront sensor 102 preferably provides aberration data 130 and iris (and pupil) image data 132 from the pupil camera 122. These data establish an aberration profile 134—e.g., a wavefront sensor spot profile, from which centroids of the spots are determined in determining the wavefront aberrations of the eye, as in Williams—and an iris (and pupil) image 136. The iris image data 132 can be similar to the iris image data 114. The wavefront sensor data 130 and the iris image data 132 also are normalized to each other, as illustrated by an overlapping reference frame 138 in FIG. 2A. The pupil can be dilated when the aberration data 130 and the image data are acquired, or can be left undilated.

Various types of refractive data can be determined and employed in developing a course of treatment for refractive surgery, such as LASIK. These data can include corneal topographic data, wavefront sensor data, corneal thickness data or other differential profiles (e.g., using ultrasound) of eye components, and other types of refractive data developed from various sources, such as from slit-scanning or optical coherence tomography techniques. For example, ultrasound can be used to measure not only corneal thickness, but also the epithelial and other eye surfaces, the amount of stromal component in a microkeratome-cut flap (for LASIK), the residual stroma under the flap, and the like. These data are typically provided on a point-by-point basis on the eye E, at varying resolutions. For example, the corneal topography data 112 from the corneal topography system 100 generally will have a higher resolution than the wavefront sensor data 130. Similarly, certain types of data are directed towards one aspect of the eye E, such as corneal surface topography data 112 mapping the surface topography of the eye E, while other data may reflect other aspects of the eye E, such as total refractive error found in the wavefront sensor data 130 from the wavefront sensor 102.

Further, the refractive diagnostic tools could be of a variety of configurations, such as a fixed, bench-type system, handheld, or multiple systems integrated into a single tool. One skilled in the art will recognize that the techniques according to the invention can be implemented in a wide variety of actual physical embodiments.

In one embodiment of the invention, these data sets are normalized to each other for more accurate generation of a refractive treatment. Here, the topography data 112 and its corresponding iris image data 114 are normalized to the wavefront sensor data 130 and its iris image data 132. For example, these two data sets are normalized to each other (illustrated by a diagram 140) based on similarities of the iris image 120 and the iris image 136 (illustrated by an iris image 142). As discussed above, this normalization may result from an overlapping of the iris images themselves, or instead from an adjustment of characteristic elements of the iris (and pupil) images, as discussed below in conjunction with FIG. 5.

In a particular embodiment shown in FIG. 2B, the aberration profile 134 is processed (e.g., via fitting Zernike polynomials, as discussed in Williams and herein) to develop wavefront aberration data shown as a pupil wavefront aberration (e.g., contour) plot 160. The wavefront sensor data 130 and the iris image data 132 (FIG. 2A) are normalized also to each other, as illustrated by an overlapping reference frame 162 in FIG. 2B. As discussed above, the pupil is preferably dilated when the aberration data 130 and the image data are acquired, and these data sets are normalized to each other for more accurate generation of a refractive treatment. The topography data 112 and its corresponding iris image data 114 are normalized to the wavefront sensor data 130 and its iris image data 132. For example, the normalization of these data is illustrated by a (superimposed) diagram 164 based on similarities of the iris image 120 and the iris image 136 (illustrated by an iris image 142) in parallel to the discussion of FIG. 2A above. The topography data 118 extends over a larger portion of the eye, such as over most or all of the cornea, while the wavefront aberration plot (or data) 160 generally extends only over the pupil or a portion of the pupil. Some correlation between the pupil wavefront aberration contour plot 160 and the topography 118, when overlapped as in or similar to the diagram 164, may be apparent, as will be appreciated by those skilled in the art even if no iris image data are used for alignment or for normalization. For normalizing or superimposing the topography and the wavefront aberration data (e.g., the topography data 118 and the pupil wavefront aberration plot 160), suitable account may be taken of the variations in optical path length (e.g., from the wavefront aberration data) or refractive index (e.g., by averaging refractive indices) of the eye in order to correlate these data, as will be appreciated by those skilled in the art.

Whether data are generated according to the procedure outlined in FIG. 2A or in FIG. 2B, as illustrated in FIG. 2C, a computer program then generates a treatment profile 144. This can be done, for example, in a stand-alone computer 104, a computer connected to the Internet or other network, or in a computational system that is part of the laser system 106, the topography system 100, the wavefront sensor 102, or other systems. The treatment generated could be a variety of treatments. For example, an irregular treatment pattern could be performed, as illustrated in the aforementioned U.S. Pat. No. 5,891,132, or a variety of other types of treatments could be performed, including, but not limited to, a variable spot size, a scanned slit, or a fixed scanned spot size laser treatment. Regardless of the treatment performed, it is generated with respect to the data 140 or 164 from the various diagnostic tools, and can be maintained normalized to the stored iris image 142.

The data from the various diagnostic tools can be used in a variety of ways to create treatments. For example, the data 130 from the wavefront sensor 102 could be solely used to create a treatment, or, instead, the data 112 from corneal surface topography system 100 could be used. Other alternative types of refractive diagnostic tool data can similarly be used solely to create treatments. Advantageous aspects of the data from the various tools could be combined to yield better overall refractive treatments. For example, the corneal surface topography system 100 returns surface topography data regardless of the amount of dilation of the pupil, but the wavefront sensor 102 may be limited by the amount of dilation present in the pupil (i.e., the wavefront sensor 102 typically only measures refractive effects of optical elements that are in the optical path). Therefore, as illustrated by the diagram 164 in FIG. 2B, the data 112 from the corneal surface topography system 100 is employed over a surface area larger than the dilated pupil, while the data 130 from the wavefront sensor 102 is used for the central portion within the area of the pupil. In both cases, the data 130 and the data 112 can be reconciled by a first spatial normalization using their respective iris images 120 and 136.

Figure 3:
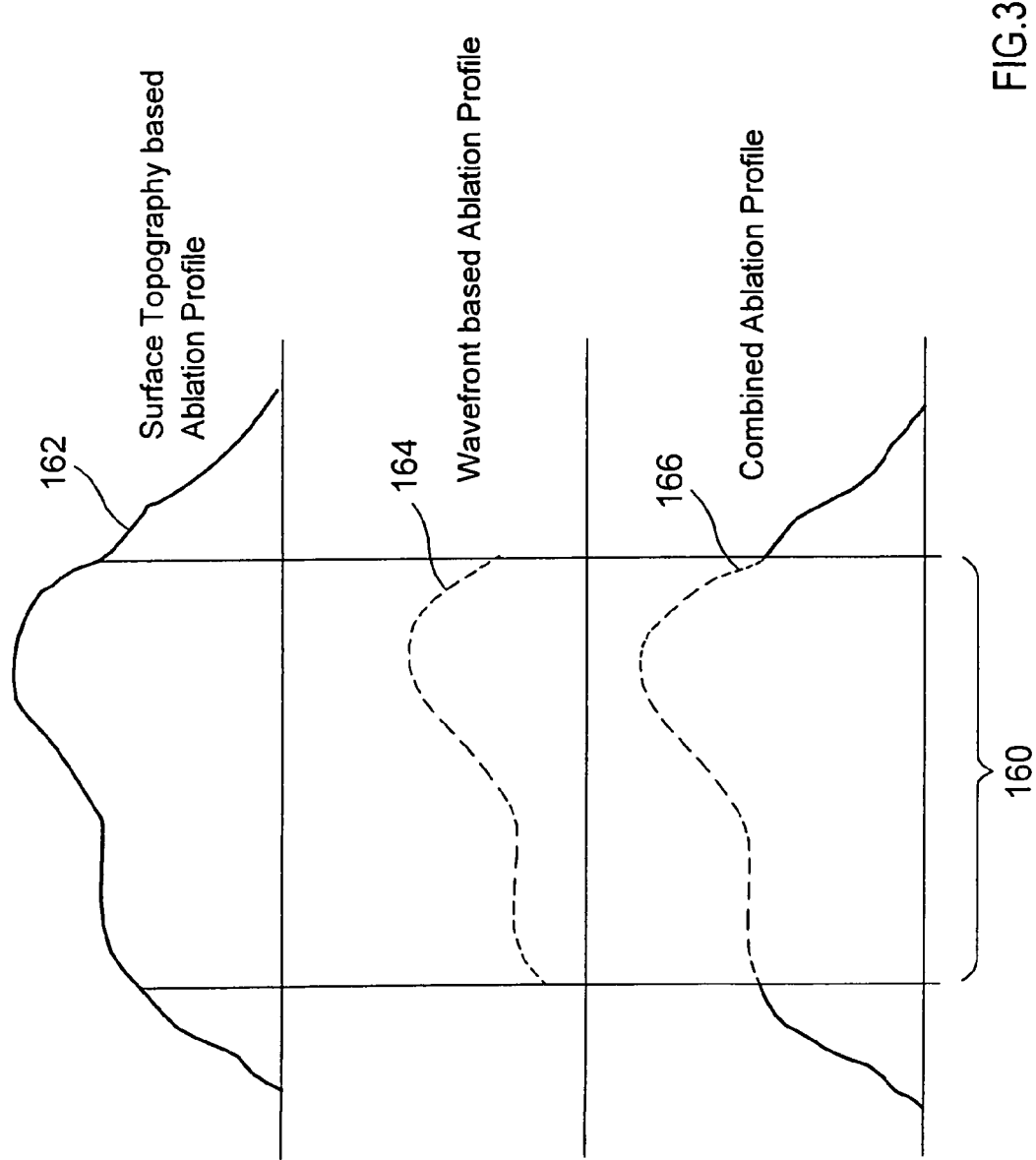
FIG. 3 is a diagram illustrating combined ablation profiles developed from wavefront data and from surface topography data.

Such a technique is illustrated in FIG. 3, in which ablation profiles based on wavefront data and surface topography data are combined. Illustrated in FIG. 3 first is a surface topography based ablation profile 162 developed from surface topography data. This data is valid even outside of the pupil, illustrated as a pupil diameter 160. To compare, a wavefront based ablation profile 164 developed from wavefront data is generally only valid within the area of the pupil diameter 160. So, the two are illustrated as a combined ablation profile 166 by using the wavefront based ablation profile 164 within the pupil diameter 160 and using the surface topography based ablation profile 162 outside of the pupil diameter 160. In this example, each ablation profile is first calculated from the corresponding data before the profiles are combined. Other techniques could alternatively combine the captured data before an ablation profile itself was calculated. Elevation-based topography systems such as the ORBSCAN II® topography system available from Bausch & Lomb/Orbtek, Inc. are especially advantageous when used with the wavefront sensor. However, other topography systems, such as curvature based systems, are also useful in the practice of this invention. Other types of systems that are useful include dual camera systems such as described in U.S. Pat. Nos. 5,159,361 and 4,995,716.

The ORBSCAN II® topography system is a slit-scan elevation based, topography system that simultaneously measures both surfaces of the cornea as well as the front of the lens and iris. Each measured surface can be displayed as maps of elevation, inclination, curvature or power. A full-corneal map of pachymetry is also derived from the measured surfaces of the cornea. Raytraced optical computations can be used to ascertain the visual effect of the various optical components within the ocular anterior segment. ORBSCAN II® topography measurements are based on diffuse reflections rather than specular reflections, to precisely detect the surface height rather than surface curvature. Use of a specularly reflected image from a placido or other reflective target to measure surface slope can be used in combination with measurement of diffuse reflections as will be apparent to those skilled in the art. For illustrative descriptions of the elevation-based, ORBSCAN II® topography system, see U.S. Pat. Nos. 5,512,965 and 5,512,966 by Richard K. Snook. Data from the ORBSCAN II® system can be accurately and seamlessly transitioned into the overall refractive data from the wavefront sensor.

It is also possible for data from the wavefront sensor to be used to "calibrate" data in the topography system. Because the wavefront sensor describes the overall refractive error in the eye, it can allow the software for the topography system to correlate a surface topography at any particular point with an overall refractive error (determined by a wavefront sensor) associated with those points. Thus calibrated, the topography system data can then be used to create an overall refractive error profile.

As another example, the data from various diagnostic tools can be combined to provide an overall model of the optical elements in the eye. For instance, a corneal surface topography system could provide surface data, an ultrasonic system could provide corneal thickness data, and a wavefront sensor could provide overall refractive error data. By "subtracting out" the effects of the surface data and the thickness data, optical elements past the cornea thus can be modeled using the various sets of data.

Figure 4:
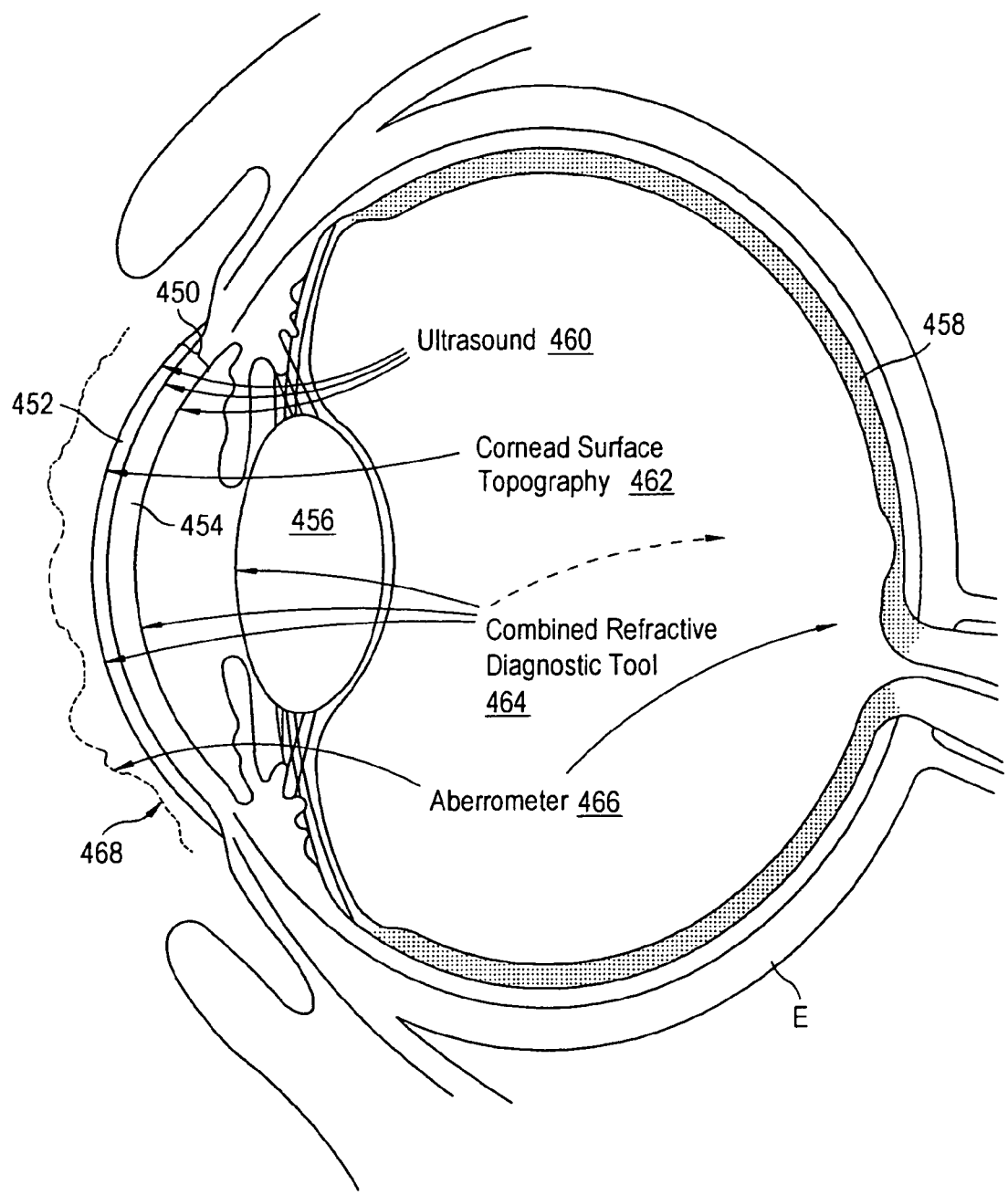
FIG. 4 is a cutaway representation of an eye, as well as associated diagnostic tools used to determine particular refractive characteristics of the eye.

Turning to Turning to FIG. 4, a cross-sectional view is shown of the eye E including a cornea 450, a lens 456, and a retina 458. The cornea 450 includes a number of layers, such as epithelium 452 and stroma 454. These various components, particularly the cornea 450 and the lens 456, combine to form an overall refractive (optical) power and a refractive characteristic for the eye E. A number of factors can contribute to refractive (e.g., wavefront aberration) errors, including, but not limited to, irregularities in the cornea 450 or in the lens 456, and the distance (e.g., in the sense of a defocusing aberration) from the cornea 450 and lens 456 to the retina 458.

Also illustrated in FIG. 4 are notations indicating various types of diagnostic tools particularly suited to analyze refractive and other characteristics of particular portions of the eye E. These tools can provide different types of data for different portions or components of the eye E. For example, ultrasonic techniques 460 can typically determine the thicknesses of the epithelium 452 and the stroma 454, which provide the overall thickness of the cornea 450. There are a variety of ultrasonic techniques that can be used, including a pachymeter as well as a technique described in U.S. Pat. No. 5,293,871, entitled "System for Ultrasonically Determining Corneal Layer Thickness and Shape," issued Mar. 15, 1994.

Corneal surface topography systems 462 typically provide and analyze corneal surface topography. Topography systems, such as the ORBSHOT™ by Orbtek and the System 2000 by EyeSys, typically exhibit a very high resolution, but are restricted to the surface of the epithelium 452 of the cornea 450.

A combined refractive diagnostic tool 464, such as the ORBSCAN II® topography system by Orbtek, typically determines and analyzes a variety of thicknesses and surfaces within the eye. This can include the thickness of the cornea 450, the surface topography of the cornea 450, the surface of the lens 456, the distance from the lens 456 to the cornea 450, and the distance from these front optics of the eye to the retina 458.

Finally, in FIG. 4, a wavefront sensor, illustrated by 466, such as the previously described wavefront sensor 102 or the wavefront sensor in Williams, provides data on the overall refractive aberrations of the eye, shown as an aberrated wavefront profile (data) 468. The wavefront sensor techniques are empirical in nature—concerned with characterizing the wavefront of light external to the eye that was reflected from the retina 458 rather than with the physical characteristics of any particular optical component of the eye E.

Referring again to FIG. 2C, based on the treatment generated 144, typically, a course of treatment, such as a series of shots, a series of scanned slits at various aperture sizes, or a variety of other types of treatment, is provided for a particular type of laser system 106. The course of treatment, illustrated by a profile 146, is itself spatially referenced to data 148 representing the iris image. The data 148 again could be an image of the iris itself, a high contrast representation in black and white of the iris, a location representation of various natural or artificially made features of the iris or cornea, or a variety of other representations of the iris. In general, the data 148 representation of the iris should be suitable to allow the course of treatment 146 to be aligned with the actual iris of the eye E when the eye E is to be treated by the laser system 106.

The laser system 106 is then loaded with the treatment profile, including the course of treatment 146 and the iris data 148. Referring to FIG. 2C, the laser system 106 can be of a variety of types, such as a 193 nanometer excimer laser, and will typically include a laser 150, an aiming system 152 (e.g., a series of optical components used to direct light from the laser 150 to the eye E), a camera 154, and a control system 156. A lower power aiming or reference beam (not shown) typically is used in conjunction with the laser 150. The aiming beam, for instance, a laser beam, can be monitored by the camera 154, which is typically an infrared camera, and can be used to aim the laser 150 as described in U.S. Pat. No. 5,620,436, entitled "Method and Apparatus for Providing Precise Location of Points on the Eye," issued Apr. 15, 1997 [PCT/EP95/01287, published Oct. 19, 1995].

In operation, the camera 154 provides an image of the iris I (see FIG. 2C) of the eye E to the control system 156, which controls the aiming system 152. The image of the iris I actually provided to the excimer laser system 106 is compared to the iris data 148 associated with the course of treatment 146. The aim of the laser head 150 is then adjusted such that the iris data 148 is co-aligned essentially with the image of iris I provided by the camera 154. This can entail translation, rotation, scaling, skew, or a variety of other transformational functions. The translation that is applied to the iris image data 148 necessary to align it with the iris I is similarly performed on the course of treatment 146, such that the ultimate course of treatment, when it is applied, corresponds to a course of treatment necessary to reduce the optical effects as predicted in the treatment generation 144.

The data of the course of treatment 146 itself can be altered, or the aim of the laser system 106 or the rotational alignment of the patient instead can be altered. Regardless of the methodology, the iris data 148 are used to align the iris I before the treatment 146 is applied.

Various types of eye surgery can benefit from the disclosed techniques. PRK can be applied to the external surface of the eye, or a LASIK procedure can be performed by first resecting a portion of the cornea and then applying laser treatment underneath. Further, the techniques can lend themselves to other, non-keratectomy-types of treatments, such as excimer keratotomy, or various types of thermal approaches to refractive correction. These courses of treatment can be accurately aligned with the iris of the eye, such that the calculated treatment pattern is provided more precisely to theoretically optimal positions.

Other benefits flow from using the iris data associated with both the diagnostic and the treatment data. For example, when a patient is in an upright position for diagnostic evaluation, sometimes the position of the eye may rotate slightly within the eye socket compared to when the patient is in a reclining position. Similarly, the patient's head alignment can affect eye rotation even when the body stays in the same position. Although the patient's brain can compensate for a slight amount of such rotation, in a highly precise correction treatment pattern for higher order defects, the change in the rotational alignment literally can rotate the eye out of position with respect to the treatment, causing a faulty treatment to be applied to the eye. The effects of such a misalignment typically are not pronounced for fairly basic courses of treatment, such as myopia and hyperopia, and even for a minor treatment of astigmatism, but with higher order defects, such as irregular astigmatism, glare, halo, and the like, the benefits of the highly precise treatment can be lost unless precise alignment with the optimal spatial treatment position is obtained and maintained. The techniques according to the invention can reduce such loss of alignment.

With respect to the iris matching and alignment itself, a variety of techniques can be employed, either using actual images of the iris or digital representations of various features of the iris. These techniques have been employed in recognition systems based on the unique features of an iris, such as U.S. Pat. No. 5,572,596 to Wildes, et al., issued Nov. 5, 1996, entitled "Automated, Non-Invasive Iris Recognition System and Method," assigned to David Sarnoff Research Center, Inc. of Princeton, N.J., and U.S. Pat. No. 4,641,349 to Flom, et al., issued Feb. 3, 1987, entitled "Iris Recognition System," both of which are incorporated by reference herein in their entirety. The former of these patents discusses scaling, rotation, and translation; the latter of these patents discusses the various features that can be used to uniquely match and identify an iris, and also discusses that a control mechanism can be used to adjust the position of the iris relative to the camera. In an embodiment of the present invention, a similar technique additionally can be used to aim the laser system 106. Similarly, U.S. Pat. No. 5,291,560 to Daugman, issued Mar. 1, 1994 and entitled "Biometric Personal Identification System Based on Iris Analysis," assigned to Iri Scan, Inc. of Mount Laurel, N.J., also incorporated by reference herein in its entirety, further discusses the "optical fingerprint" provided by the iris. The pattern matching and feature matching techniques of these patents and otherwise known to the art are employed for alignment purposes rather than strictly identification purposes.

Alternatively, or in addition, the camera 154 of the laser system 106 can receive an image of the iris I which is then displayed on a screen. The iris image data 148 can then be superimposed to allow the physician, technician, or other healthcare worker to manually aim or adjust the laser system 106, or to manually verify the aim of the system 106.

Figure 5:
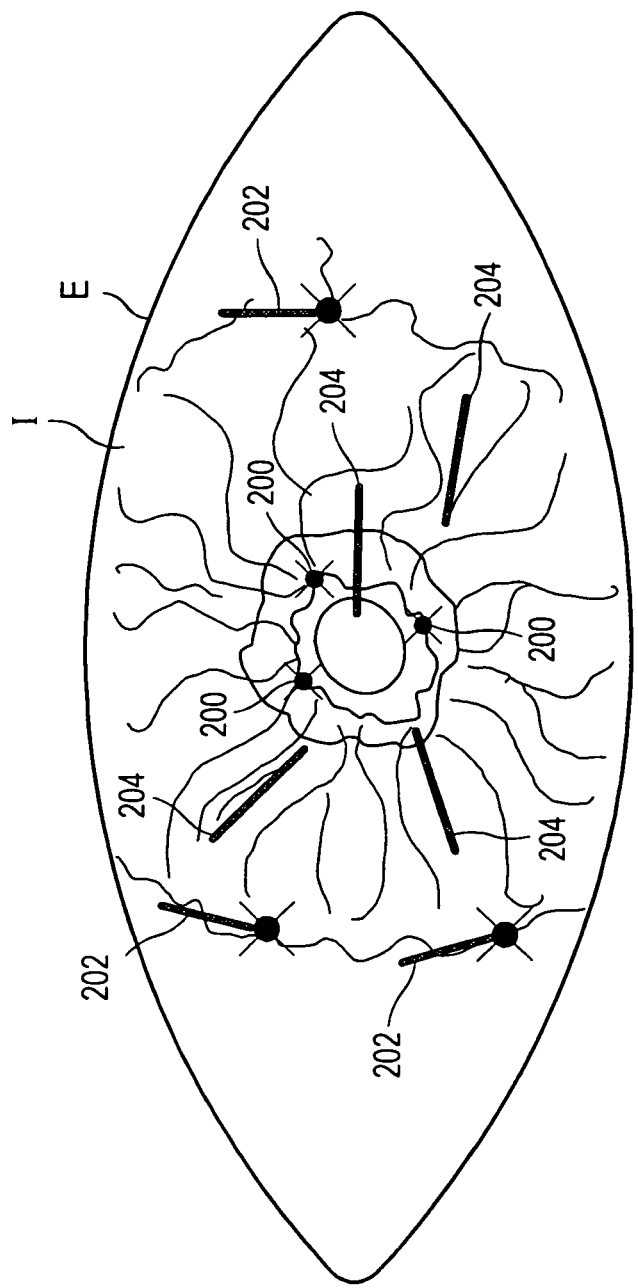
FIG. 5 is a diagram illustrating various features of an eye that can be used as characteristic iris data in a system and method according to the invention.
Figure 5A:
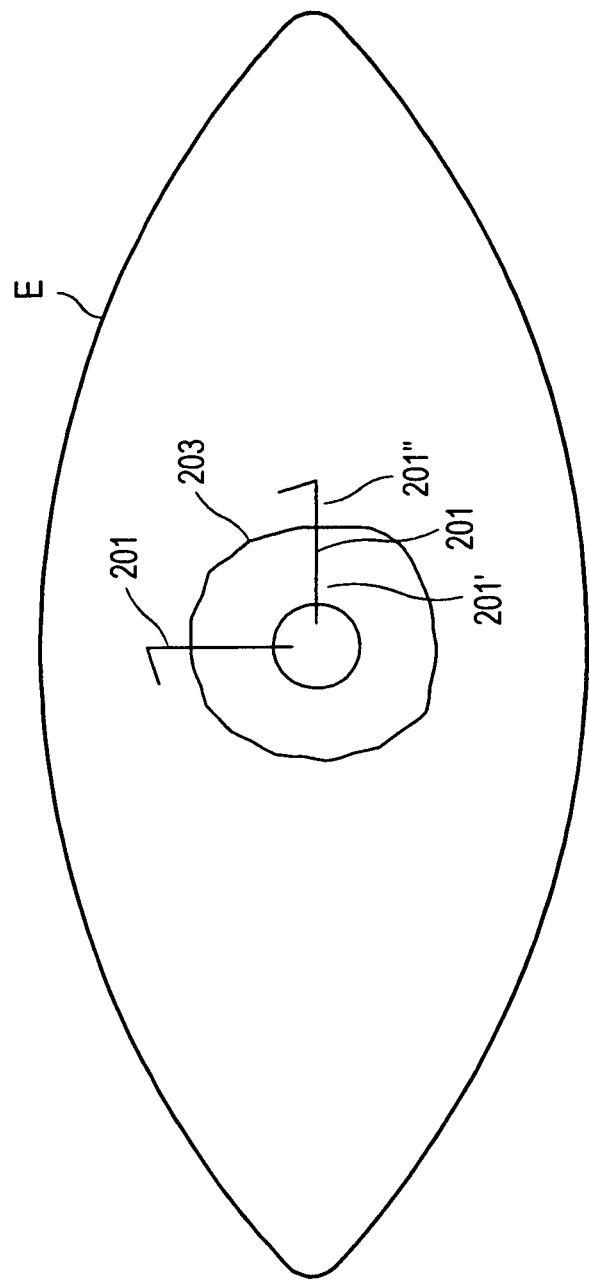
FIG. 5A is an eye diagram similar to FIG. 5, showing a marker according to an embodiment of the invention.

Referring to FIG. 5, the iris I of the eye E is illustrated in more detail, showing how particular features can be employed for matching the patient's eye E for treatment with his or her previously stored iris I image. For example, a set of points 200, defining generally circular features such as collarattes, can be employed as descriptors, as can concentric furrows 202 or radial furrows 204. Other features that can be used are generally described in the above-referenced U.S. Pat. No. 4,641,349 to Flom, which include pigment spots, crypts, atrophic areas, tumors, and congenital filaments. Similarly, the pupil can be used in iris matching as well, for example, as a center reference point from which iris features then define the rotational position of the eye. Fewer or greater features can be employed, for example, depending on the complexity of the treatment to be applied. If the treatment is rotationally symmetrical, such as a treatment for pure myeropia or hyperopia, rotational displacement is of no consequence, so the center point can be located with respect to the pupil. But with greater complexity of treatment, more detailed features can be employed for more precise registration of the eye E before treatment. Alternatively, artificial features can be imposed upon the eye E, for location, including in the iris area. For instance, three laser marks can be created on the eye E if the treatment is to occur before the laser marks would heal. A marker in the form of thermal marks made, for example, with a Holmium laser would provide information about rotation and translation of the eye prior to and during surgery. Various marker shapes are also envisioned. As shown, for example, in FIG. 5A, radially extending markers 201 could provide eye movement and alignment data. As shown, reference 203 denotes, e.g., a scleral boundary or alternatively, a gray-scale profile determined from an iris recognition program such as that provided by Sensomotoric Instruments, Teltow (Germany). The markers 201 have a proximal segment 201' beginning around the approximate center of the eye E and a distal segment 201" that deviates from being collinear with segment 201'. It can be seen that radial marker 201 traverses the boundary 203. It will be appreciated also that a marker should have sufficient range to be seen during the refractive procedure; i.e., after the flap is lifted in a LASIK procedure, for example. Alternatively, the marker could consist of a suitable dye, particularly one visible or detectable in infra-red light to be viewed by an infra-red camera. The dye could further be used as a tattoo by e.g., coagulating the dye after application or coagulating the dye and applying it to shrinked collagen. Still further, a combination of dye and special glues could be used. Such a dye or dye-based market should be visible/detectable for the duration of the refractive procedure. In cases where the pupil is dilated, the marker should remain visible/detectable for at least 15 minutes, preferably up to an hour, after its application. This is due to the finding that dilation induces ocular aberration and sufficient time should pass for the dilation-induced aberration to subside. Then, the diagnostic steps can be taken and the treatment followed soon thereafter. Further, other identifying portions of the visible surface of the eye can be used, apart from the iris I. In all of these techniques, features of the visible portion of the eye E are employed for registration between the diagnostic system, the developed treatment, and the actual treatment as applied to the eye E.

Figure 6:
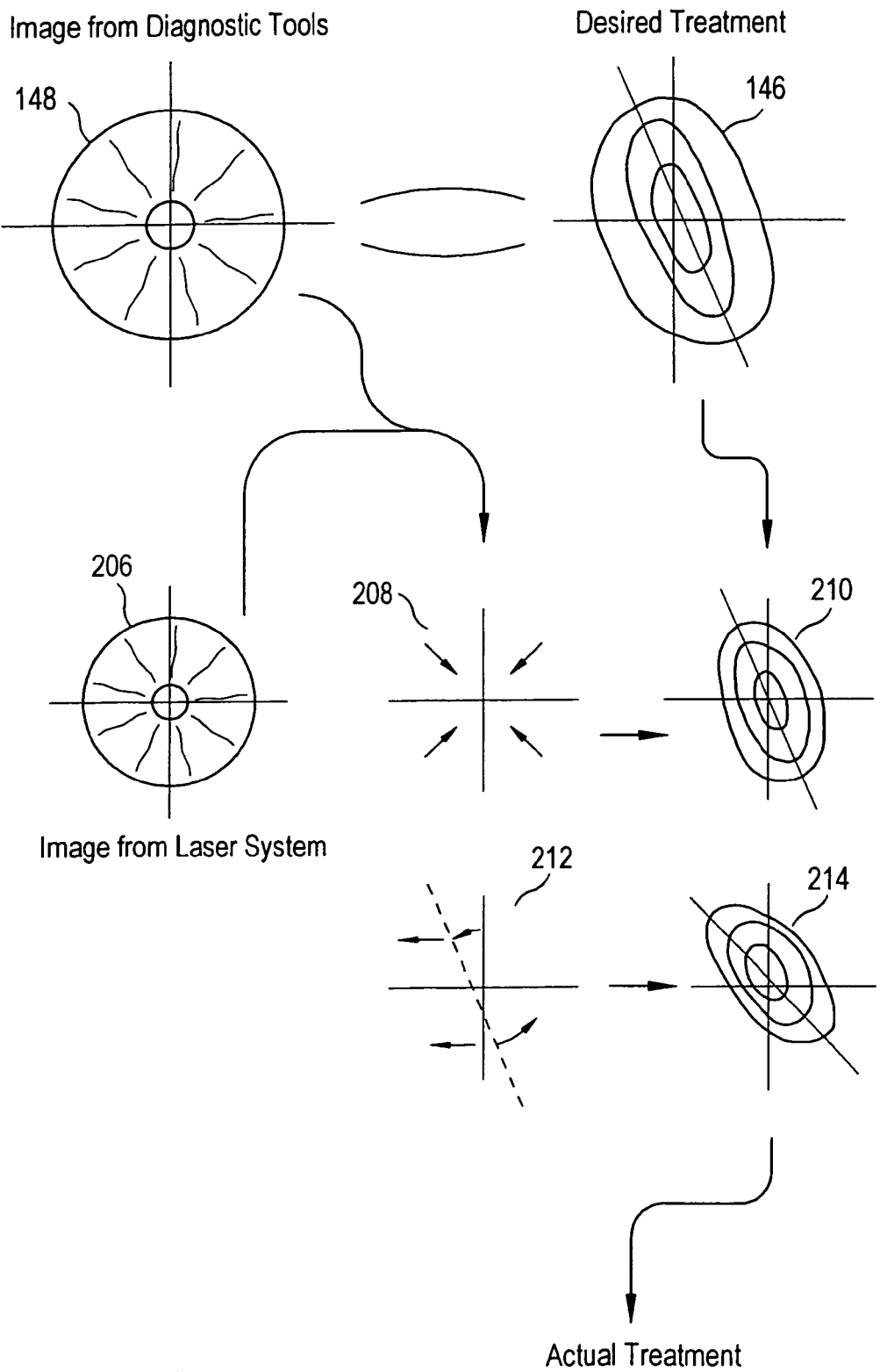
FIG. 6 is a flow diagram illustrating the use of stored iris data and imaged iris data to translate a desired treatment into an actual treatment according to the invention.

Turning to FIG. 6, various adjustments that can be made to the desired treatment based upon the image of the actual iris I as received by the laser system 106 are illustrated. Referring again to FIG. 2C, the treatment generated 144 is provided as a desired treatment pattern 146 for controlling the laser system 106. The associated reference iris image data 148 from the diagnostic tools is used to align the treatment pattern 146 with the patient's eye E. The iris image 206 is provided by the pupil camera 154 of the laser system 106 and provided to the control system 156. The control system 156 compares the image 148, or the descriptors derived from that image, to the iris image 206. Based on the comparison, a variety of scaling functions is applied to the desired treatment 146. For example, it may be determined, based on the overall size of the actual iris image 206, that the treatment should be reduced in scale because of different focal distances of the diagnostic tools 100 or 102 and the laser system 106. So a scaling 208 is calculated and applied, yielding a scaled treatment 210. Then, it may be determined that the now scaled, desired treatment 210 must both be translated and rotated, as indicated by a translation and rotation function 212. This in turn is applied to the scaled desired treatment 210, yielding the actual treatment 214. These data are then used by the laser system 106 to perform an actual treatment.

Alternatively, if the control system 156 has great enough computational power, it is possible for each shot (i.e., laser pulse) to be appropriately rotated and translated. This may be desirable if the eye E displays a large degree of dynamic rotation and movement during the treatment, for example. Then, the iris image 206 can be tracked and the scaling functions 208 and 212 illustrated in FIG. 6 applied dynamically to each specific shot or sequence of shots in the desired treatment pattern 146. In this manner, the movement of the eye E can be accommodated shot-by-shot. This technique can be combined with the aiming laser technique of PCT/EP95/01287 such that the exact placement of each shot or series of shots relative to the iris image 206 is determined before the shot or shots are applied.

Therefore, in embodiments of the invention, any of a variety of diagnostic instruments can be fitted with a camera or other imager that acquires an image of the pupil, the iris, or other distinctive characteristics of the exterior of the eye and exports data corresponding to that image. Then, when a refractive treatment, such as an excimer laser treatment used in LASIK, is performed, the stored image (or its distinctive components) is compared to the actual image of the pupil, iris, or eye to align the laser such that the treatment will fall precisely as calculated.

In an exemplary embodiment of the invention, a method of eye alignment and characterization is described as follows.

A marker is provided in a selected region of the patient's eye. Various marker types and shapes are described elsewhere in the description and include, but are not limited to, thermally induced marks, radial markings, and dye markers. A first image of the patient's eye is acquired with the pupil undilated, thus the image includes an image of the iris and the marker. Preferably, the image is an infra-red image acquired with an infra-red camera, however, a visible light image is also suitable. Thus, the marker will be suitably visible and/or detectable in infra-red light. The pupil is then dilated by light intensity variation or chemically, and a second image of the eye, including the dilated pupil and marker is acquired. A diagnostic measurement of the eye in the dilated state is obtained, the diagnostic measurement preferably being a wavefront aberration measurement or, alternatively, a topographic or other refractive diagnostic measurement. A computer system is then used to develop a photo-refractive treatment from the diagnostic measurement for refractive correction of the patient's eye. If a dye is used as the marker, it is preferable that the dye remain visible and/or detectable for at least 15 minutes, preferably up to an hour, after application of the dye or for a sufficient time for dilation-induced aberrations to subside.

According to the invention, the method finds further utility by aligning the second image with the first acquired image, preferably by comparing the markers in the respective images or, alternatively, by comparing other corresponding characteristic features in the respective images. Similar to other aspects of the invention described herein, development of the photo-refractive treatment is accomplished by aligning the diagnostic measurement with the marker on the patient's eye. In an aspect of the invention, the alignment procedure may incorporate iris pattern recognition provided through the computer system. Various iris pattern recognition software is known in the art and is commercially available.

The practitioner has the option of implementing the developed photo-refractive treatment in a real time sequence immediately following acquisition of the second image. In this case, the eye image includes the dilated pupil, thus no iris pattern from the second image can be compared to and aligned with the iris image of the first acquired image. Consequently, the markers are used in the respective images to correlate, normalize, or otherwise align the images and the refractive or diagnostic tools associated with those images. Alternatively, photo-refractive treatment of the eye may be delayed for hours, days, etc. and performed electively. In this case, another image of the patient's eye, including an image of the iris will be acquired preferably by a refractive tool such as, for example, a photo-ablative laser system including a pupil or iris camera, preferably an infra-red camera, for acquiring the image. Prior to treatment, that image will be aligned with the first acquired iris image and in conjunction with the developed treatment, based upon the diagnostic measurement. Of course, through image storage, digitization, etc., alignment of the developed diagnostic treatments, the diagnostic tools, the refractive tool or any combination thereof can be verified and such alignments can conveniently be displayed to the practitioner though a display system.

A system for performing the alignment and photo-refractive treatments discussed above includes most basically a first camera used to acquire the first image which includes an iris image of the eye, a refractive diagnostic instrument for making a wavefront, topography, pachymetry or other refractive diagnostic measurement as one skilled in the art will appreciate, a laser system capable of providing the developed photo-refractive treatment that preferably includes a second camera used to acquire another image of the eye, a computer system used for developing and aligning the photo-refractive treatment linked to the laser system, the first camera and the diagnostic tool, and a control system attending to implementation of the photo-refractive treatment that is suitably linked to other components of the system. In an aspect of the invention, a second refractive diagnostic instrument that further includes a camera which is used to acquire a further image of the eye that includes an iris image can also constitute a component of the overall system. A display system can also advantageously be linked to the overall system.

Figure 7:
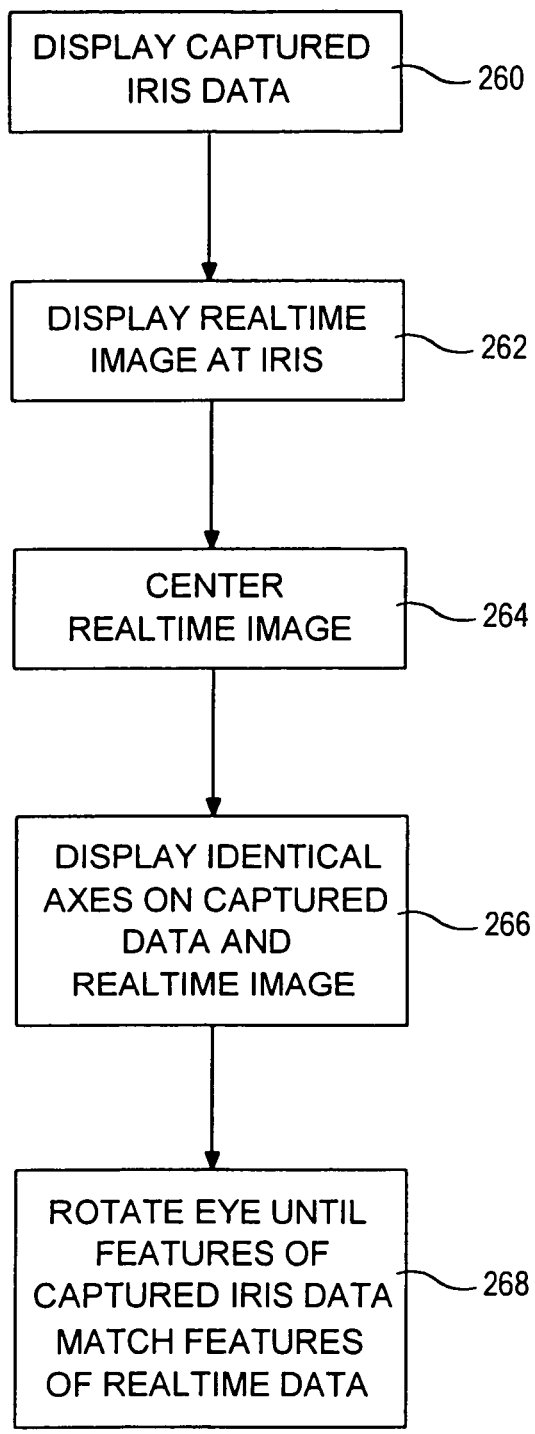
FIG. 7 is a flow diagram illustrating an alternative technique employing stored iris data to align a treatment.
Figure 8A:
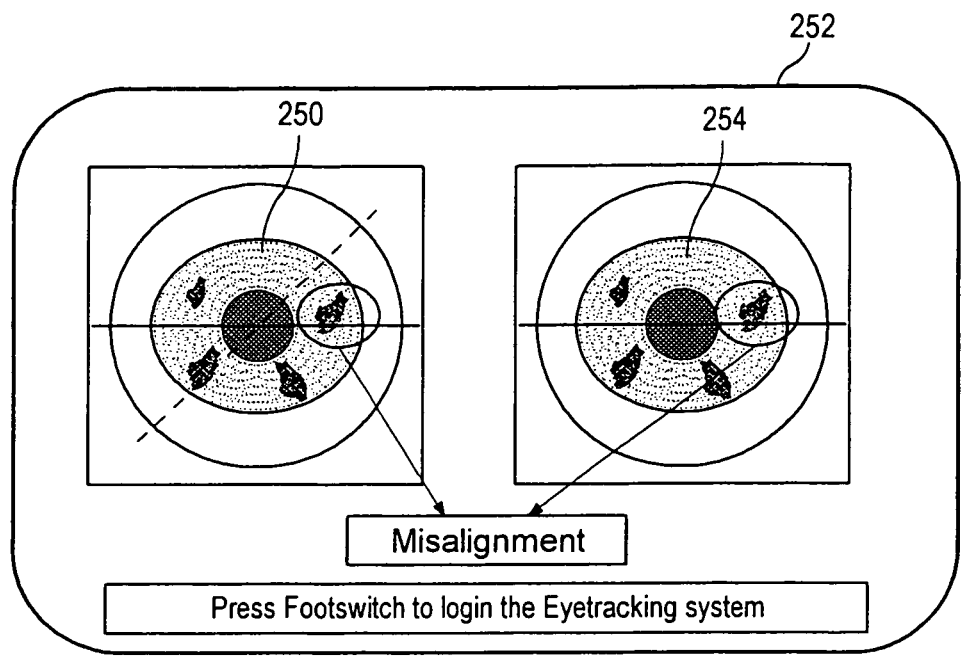
FIGS. 8A and 8B are display images illustrating the technique of FIG. 7.
Figure 8B:
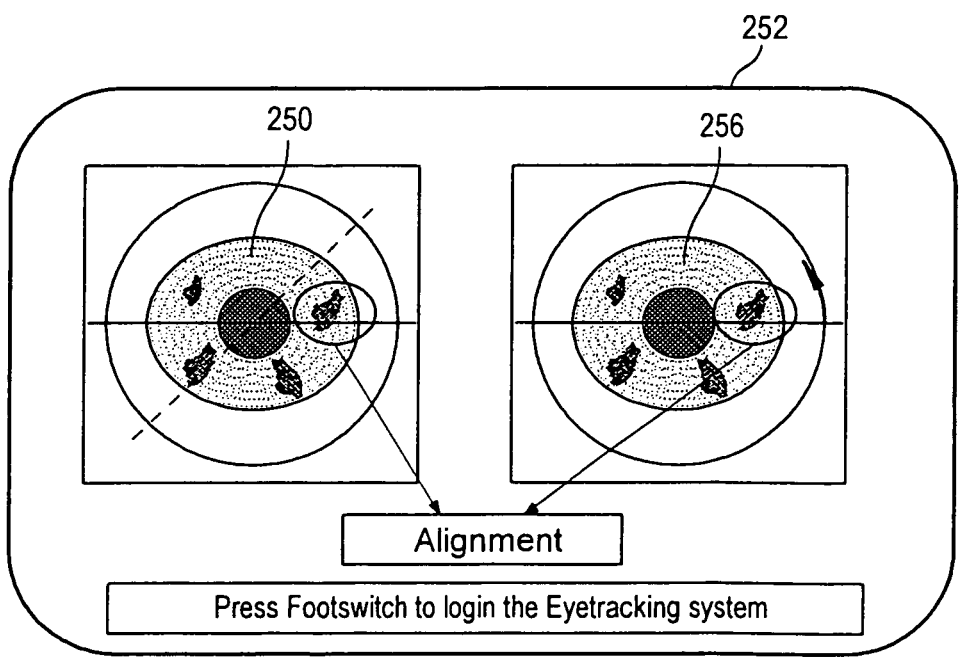

Turning to FIGS. 7 and 8A-8B, shown is an alternative technique to employ a previously captured image of an iris I to insure appropriate alignment of a laser treatment with the calculated treatment profile. Generally, FIG. 8A illustrates a display 252 provided by the camera 154 of the laser system 106 in FIG. 2C. On the left is captured iris I image data 250 captured when a refractive diagnostic tool was used to determine the refractive characteristics of the eye E. From this data, and coaligned with this iris I image data 250, a treatment profile had been developed. On the right side of the display 252 is real time iris I image 254, which is returned by the camera 154 of the laser system 106. As can be seen, the real time image 254 is slightly rotationally misaligned compared to the captured image data 250. This provides the physician with an opportunity to realign the patient's eye E, yielding in FIG. 8B a properly aligned real time iris I image 256. Preferably, the display includes reference axes that allow the physician to easily determine rotational misalignment. The system could also provide, for example, a cursor that the physician could place over identifying features to determine precisely the rotational location relative to the axis.

FIG. 7 illustrates the steps of using the system of FIGS. 8A and 8B in aligning the iris. First, the captured iris I image data 250 is displayed in a step 260. Simultaneously, the real time image 254 of the iris I is displayed at a step 262. When the excimer laser system 106 is a Keracor 217 employing an eye tracker, the physician then activates the eye tracker at a step 264, which centers the real time image 254. The eye tracking system on the Keracor 217 provides for centering the iris I, but does not provide for rotational alignment of the iris.

Proceeding to a step 266, an axis is displayed on both the captured data 250 and the real time image 254. The physician then compares the images on the screen, and determines an amount of rotation necessary to align the two images of the iris I. The physician then rotates the eye E so that the real time iris I image 256 rotationally corresponds to the captured iris image data 250. The physician can do this manually, such as using a suction ring or by repositioning the patient's head. Further, the system can provide for a "virtual" rotation of the patient's eye E by rotationally translating the treatment profile by an amount specified by the physician. In any case, the eye tracking system first provides for centering of the real time iris I image 254, and the physician then effects the rotational alignment of the iris I image 256 compared to the captured image data 250.

Figure 9A:
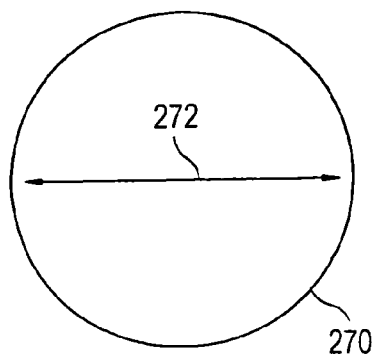
FIGS. 9A and 9B are diagrams illustrating a laser alignment beam/imaging system alignment technique according to the invention.
Figure 9B:
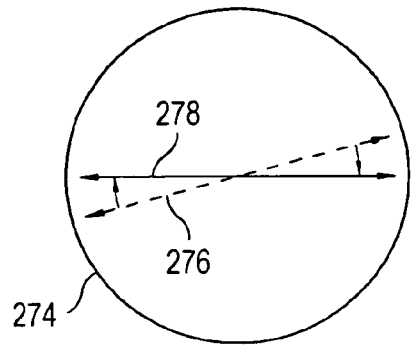

Referring to FIGS. 9A and 9B, a technique for developing the axis as illustrated in FIGS. 8A and 8B is shown. Specifically, as in FIG. 8A, an iris image 270 is shown corresponding to an axis in the laser system. In this case, an axis 272 is created by rapidly scanning the aiming system with its visible aiming beam left to right over the X axis. Thus, when the doctor views the image of FIG. 8A, the axis on the real time iris I image 254 is created by the aiming system of the laser itself, which is the same aiming system used to aim the beam. Therefore, the true X axis of the laser will be known because the aiming beam scanned by that aiming system is creating that X axis.

Turning to FIG. 9B, a further technique is illustrated for aligning the aiming system of the laser with the display or optical system. Assume in FIG. 9B that again the pupil 274 is shown in the optical system of the laser or on the eye tracker camera of the laser, but that the aiming beam is scanning over a line 276, which is not exactly aligned with the X axis of the optical system or the eye tracker. A technician can align the scanned aiming beam 276 with the X axis of the optical system and the eye tracking system, rotating the scanned aiming beam 276 to the true X axis 278 of the optical system and the eye tracking camera. Then, a line can be superimposed on the eye tracking system, or a line can be formed in the optical system that corresponds to the true X axis of the laser's aiming system. Further, this alignment can be periodically verified by scanning the aiming beam on the X axis and ensuring that that scanned aiming beam matches with the alignment axis within the optical system or on the eye tracking system video display. Translational X-Y alignment can be similarly adjusted and verified.

Figure 10:
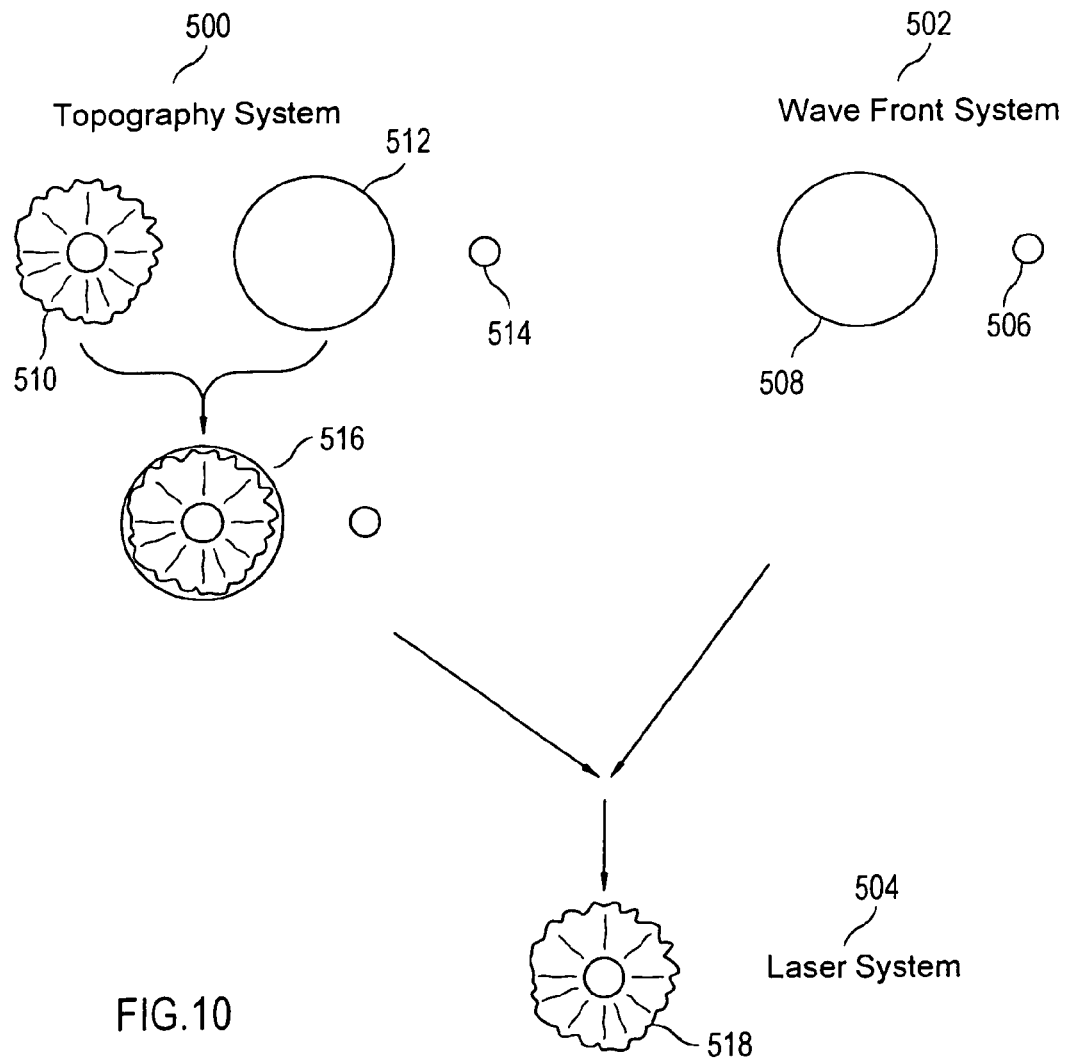
FIG. 10 is a diagram illustrating alternative alignment techniques according to the invention.

Use of Multiple Types of Data to Align Multiple Diagnostic and Treatment Systems Turning to FIG. 10, another technique is illustrated in which not only iris Iimage data is captured, but also other types of data in order to align the captured refractive data or treatment profiles among various systems. Specifically in FIG. 10, illustrated is alignment data captured by a topography system 500, a wavefront system 502, and a laser system 504. If the wavefront system 502 has difficulty capturing iris I image data, or it is desired to fully dilate the eye before capturing the wavefront data, the disclosed techniques can allow alignment without such data. In that case, in one embodiment, the physician first makes a reference mark 506 on the eye. That reference mark 506 then acts as a rotational alignment marker relative to an outline of the iris 508. The wavefront system encaptures the wavefront aberration data along with the pupil outline data 508 and the reference mark 506.

Then, the topography system 500 is employed. The topography system 500, however, does capture the iris image data as illustrated by the iris image data 510. It also captures the outline of the iris 512 as well as the previously made reference mark 514, corresponding reference mark 506. These two are simultaneously captured as illustrated by the image 516, and thus the topography system 500 maintains a translational and rotational reference between the iris image 510, the iris outline 512, associated reference mark 514, and the capture topography data itself. Further, the topography system 500 can combine its data with a wavefront system 502 based not on the iris image 510, but instead on the outline of the iris 512 and the rotational reference mark 514. That is, the topography system 500 and wavefront system 502, when their data is combined to develop a course of refractive correction, align their data based on the captured iris outlines 512 and 508 as well as the rotational reference marks 514 and 506.

Preferably the iris image 510 is also stored so that when the course of treatment is calculated, it can be referenced to that iris image 510. Then, that iris image 510 is used by the laser system 504 to align to a real time iris image 518 captured by the laser system 504.

Thus, the laser system 504 employs the iris image 518 itself, the wavefront system 502 employs the outline of the iris image 508 with a reference mark 506, and because the topography system 500 employs both, both the initial diagnostic data between the topography system 500 and the wavefront system 502 can be co-aligned, as well as the treatment profile based on that data when the ablation is performed by the laser system 504.

This may be particularly useful when the topography system 500 and wavefront system 502 are initially employed to capture diagnostic data and only later is the laser system 504 employed. A temporary reference mark that is captured as the reference marks 514 and 506 can be applied to the eye, such as with the medical pen. Although that mark may be gone when the laser system 504 is later used, because the iris image 510 was captured along with that reference mark 514 by the topography system 500, the laser system 504 can employ its own captured iris image 518 to align the treatment.

Figure 13:
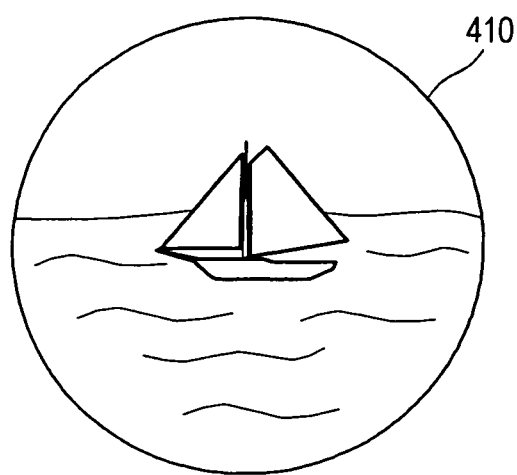
FIG. 13 is a diagram of an exemplary fixation image for use in the wavefront sensor of FIG. 12.

Further, it is possible that the reference mark itself would not be needed. If the wavefront system 502 and topography system 500 are either simultaneously employed or employed without movement of the patient's eye or head, then it may be assumed that the proper rotational alignment is maintained. Then, the wavefront system 502 need only capture the outline of the iris 508 and associate that with the outline of the iris 512 captured by the topography system 500. This can be achieved by fixing the patient's eye, or by fixing the patient's head and moving the two diagnostic systems into position without the patient's head moving. If this technique is used, it may be further desirable to employ a rotational reference image, such as illustrated by the sailboat below described in FIG. 13, to further ensure rotational alignment between the eyes when the wavefront system 502 and the topography system 500 is used.

Figure 11A:
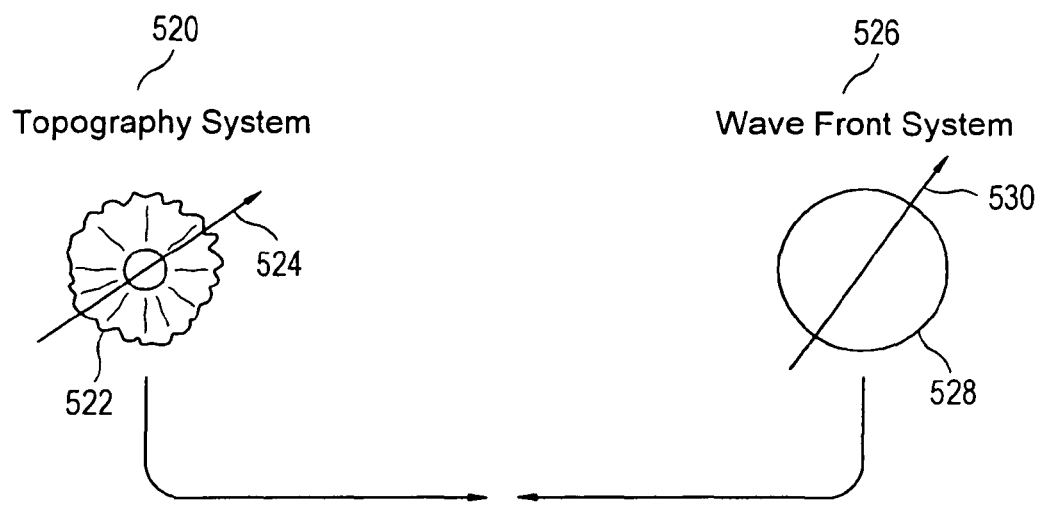
FIGS. 11A and 11B are further refinements of alignment techniques according to the invention.
Figure 11B:
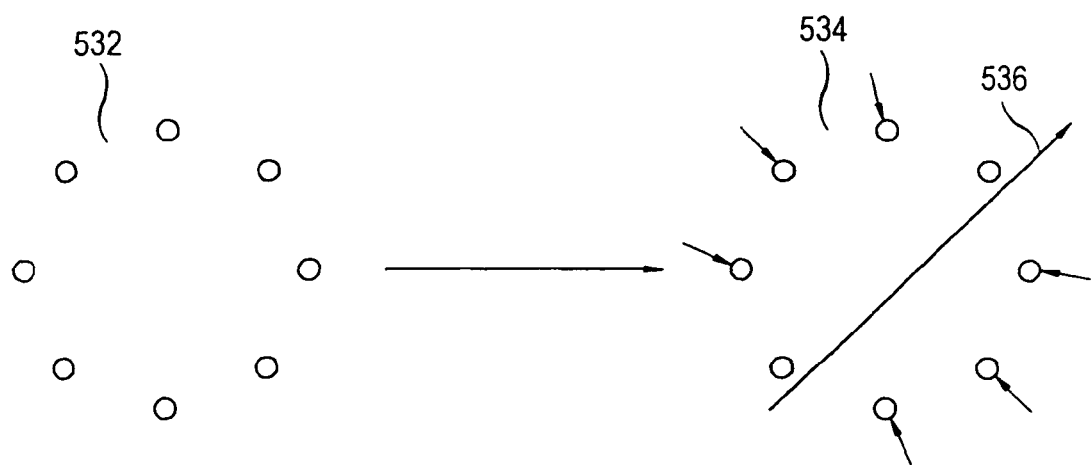

A variety of permutations of this arrangement are possible. Referring to FIG. 11A, a topography system 520 captures iris data 522, but also as part of its analysis captures an axis of astigmatism 524. Then, a wavefront system 526 also captures wavefront data but not an iris image, but does detect the outline of the iris as illustrated by the circle 528. The wavefront system also captures an axis of astigmatism 530. Then, those axes of astigmatism are used to co-align the data captured by the topography system 520 and the wavefront system 526. As a alternative of this technique, illustrated in FIG. 11B, a ring of illumination diodes 532 is installed on the wavefront system 502. The reflections of these diodes, illustrated by an image 534 is captured by a pupil camera of the wavefront system 502. Based on the distortion of positions of those illuminations of the illumination diode ring 532, as captured by the image 534, again an axis of astigmatism 536 is captured to be associated with the axis of astigmatism 524 captured by the topography system 520. This provides an additional basis with which to co-align the data from the topography system 520 and the wavefront system 526. Further, in this case, the axis of astigmatism can both be based on the astigmatism created by the surface of the eye, rather than the overall refractive error of the eye as captured by the wavefront system 526 wavefront ablation profile.

Other alternatives include a system in which the two images are superimposed. Further, a variety of user interface tools can assist the physician, including the aforementioned cursor positioning and the software rotation of the treatment profile.

Further, the use of iris data or other alignment data need not be continuous. The iris data can be used as an initial alignment tool, and then other simpler alignment techniques can be used throughout a course of diagnostic analysis or refractive treatment, such as the location of the iris alone. That is, the iris data can be used to establish the rotational alignment, and then the outline of the iris can be used to maintain translational alignment during a treatment. Further, the rotational alignment can be periodically "spot checked" throughout a refractive analysis or treatment, dependent upon processing power, even while translational alignment is maintained based on the outline of the iris itself.

Patient and Eye Validation

As an additional side benefit, when the patient lies down and the iris I image (FIGS. 2C and 5) is acquired, the iris matching algorithm can determine not only the translation, scaling, rotation, and skew to match the actual iris image 206, but can also validate the eye E that is being operated on. The iris-matching algorithm thus acts as a failsafe mechanism to ensure that a particular laser treatment is in fact the appropriate treatment for this patient rather than another patient. Similarly, it acts as a failsafe mechanism to ensure that the proper eye E is being operated on, as even the two irises of a single patient have different descriptive features. These failsafe mechanisms are especially useful in distributed systems, where the diagnostic information is acquired at a first location, the treatment is developed at a second location, which is subsequently applied at a third location. The system can provide a warning if it cannot match the features of the iris.

Like aiming of the laser system 106, validation can be done automatically or manually, using a display with the iris image data 148 superimposed over the iris image from the camera 154.

Wavefront Sensor

Figure 12:
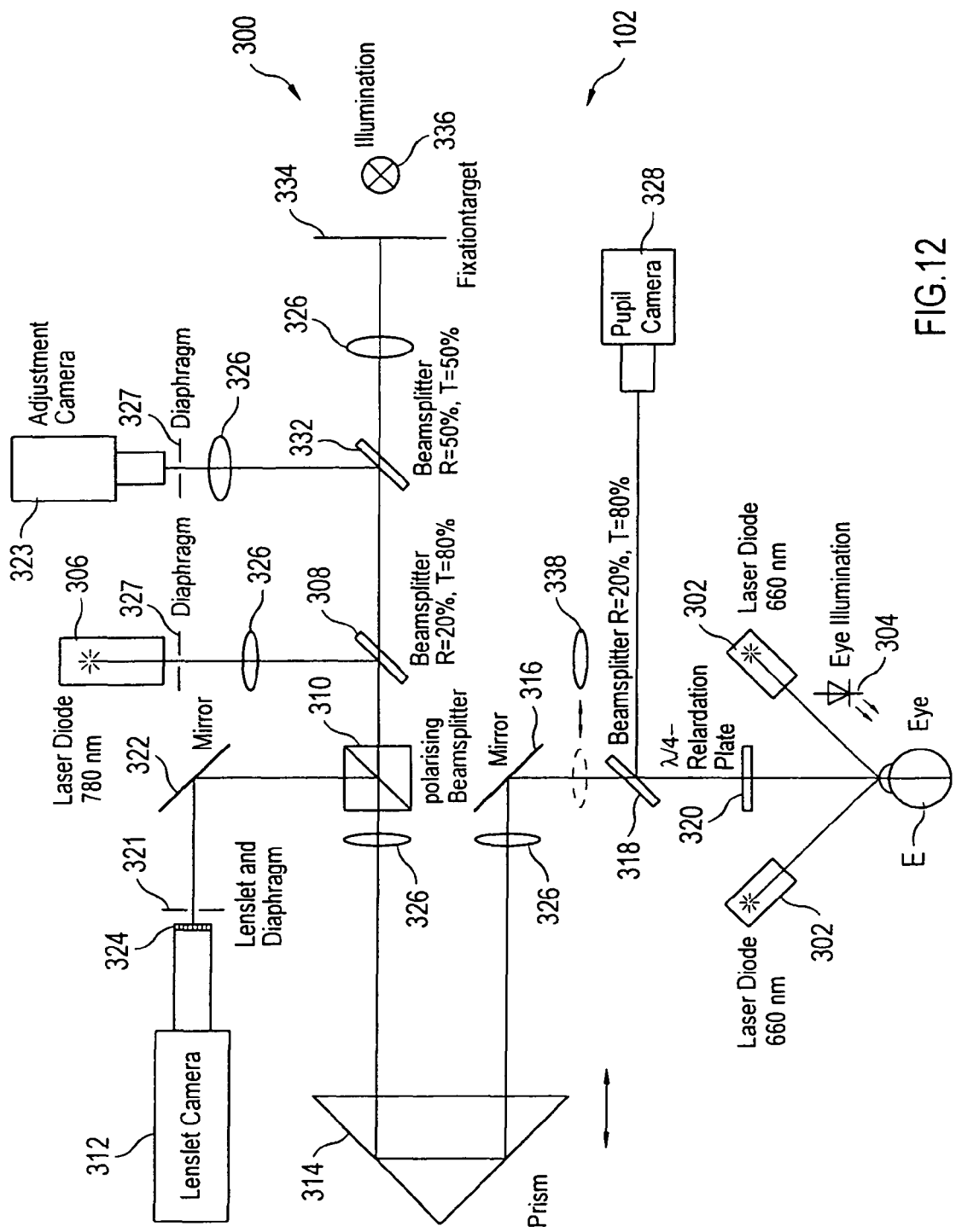
FIG. 12 is a block diagram of a wavefront sensor for use in a system according to the invention.

Turning to FIG. 12, a block diagram of a preferred wavefront sensor 300 is illustrated. The wavefront sensor 300 is similar in concept to the wavefront sensor of Williams, but includes certain features that make it especially useful for receiving iris data and for sharpening the focus of light spots on a sensor used in determining the wavefront aberrations of the eye. In general, the wavefront sensor 300 focuses or scans a light (typically a laser) on the retina of an eye and then analyzes the light returned (i.e., backscattered from the retina) through the lens and corneal optics of the eye and imaged by a lenslet array. Based on optical aberrations in the eye's optics, the system develops an overall wavefront aberration analysis from the returned light. Generally, to perform the analysis, the returned light becomes aerial images formed by a lenslet camera on a sensor of the lenslet camera. From these images, the wavefront sensor develops a wavefront aberration map of what corrections are necessary to the eye's optics that would yield emmetropic, or very nearly emmetropic, vision.

To properly orient the patient's eye E, two 660-nanometer laser diodes 302, shown in FIG. 12, can be aligned at angles to the eye E. When spots on the patient's eye E from the laser diodes 302 are merged into a single spot, by appropriate adjustment of the wavefront sensor 300 (or 102), the output beams of the laser diodes 302 (or optics directing these beams), the patient, or otherwise, the eye E is positioned at, or approximately at, a precise focal distance from the wavefront sensor 300 (or 102). Alternatively, the patient's eye E can be properly oriented by a physician, technician, or other healthcare worker by visually looking at an iris image of the eye E to find the correct focal distance from the wavefront sensor 300 to reduce the overall exposure on the eye E. In this case, there is no need for the laser diodes 302. A light source, eye illumination 304, provides light for a pupil camera 328 discussed below.

Once the eye E is properly aligned, it receives light from a light source 306 (e.g., a laser diode, such as a 780-nanometer output laser diode) along an optical path to the eye E. Preferably, the laser diode 306 has more than one output power setting (i.e., two-power or multi-power modes), at least one at lower power for alignment and initial focusing and at least one at higher power for creation of a multi-spot image in a sensor (e.g., a lenslet camera) 312 discussed below. For example, typical lower and higher powers are 0.5 µW and 30 µW, respectively. These powers depend upon a number of factors, such as how long the laser diode 306 is to remain turned on at higher power.

A portion of the beam from the laser diode 306 first reflects from a beamsplitter 308 (e.g., 80% transmittance, 20% reflectance). The reflected beam passes through a polarizing beamsplitter 310, which ultimately improves the signal to noise ratio (or signal intensity) of light backscattered from the retina of the eye that is eventually detected by the lenslet camera 312, as discussed below. The beamsplitter 310 polarizes the light received from the laser diode 306, generally passing light linearly polarized along one direction and reflecting light not polarized in that direction. The polarized light is then passed through a trombone-type prism 314 which is used to adjust the focus of the light from the laser diode 306 onto the retina of the eye E, at which point light backscattered onto the lenslet array from the light impinging on the retina will also be correctly or nearly correctly focused. The light from the trombone prism 314 is reflected from a mirror 316, passed through a beamsplitter 318 (e.g., 20% reflectance, 80% transmittance), and then through a $\lambda/4$ waveplate 320. The $\lambda/4$ waveplate 320 is oriented to produce substantially circularly polarized light from the linearly polarized light. The significance of this will be appreciated in the discussion below of backscattered light returned (the "returned light") from the eye E to the polarizing beamsplitter 310.

After passing through the $\lambda/4$ waveplate 320, the light is then focused onto the retina of the eye E. The light is backscattered or reflected from the retina and the backscattered light spot on the retina then passes back through the optical components of the eye E, such as the lens and the cornea. On the return path, the circularly polarized image light is retarded again by the waveplate 320 to yield light linearly polarized perpendicular to the incoming linearly polarized light formed on first passage through the waveplate 320, as discussed above. A portion of the perpendicularly polarized light then passes through the beamsplitter 318, reflects from the mirror 316, passes back through the prism 314, and returns to the polarizing beamsplitter 310. At this point, all or most of the light is perpendicularly polarized, and is thus substantially reflected by the polarizing beamsplitter 310 and then reflected by a mirror 322 into the lenslet-imaging camera 312. To get some of the returned light into an adjustment camera 323, discussed further below, the waveplate 320 can be tilted and/or rotated from its optimal orientation (e.g., rotated by approximately 5 degrees). In this implementation, the light received by the adjustment camera 323 would have a polarization substantially perpendicular to the returned light. Other schemes besides tilting (or rotating the waveplate 320 from its optimal orientation for providing returned light to the adjustment camera 323, including changes to the optical path and optical components of the wavefront sensor 300 (or 102), are envisioned and are included within the scope of the present invention. For example, the mirror 322 instead could be a device having a controllable transmittance and reflectance, such as a liquid crystal device, and the adjustment camera and any focusing optics can be positioned to receive a fraction of the returned light that is transmitted by the controllable device. In such an implementation, the beamsplitter 308 would be unnecessary and the light received by the controllable device would have substantially the same or parallel polarization as the polarization of the returned light.

The lenslet camera 312 is preferably a charged couple device (CCD) camera, such as a TM-9701 manufactured by Pulnix, which includes an array of lenslets 324, although other types of cameras and other sampling optics analogous to the lenslet array 324 (including optics separate from a camera) could be used. For example, an ICX 039DLA camera by Sony Corporation can be used for both the lenslet camera 312 and the pupil camera 328. The lenslet array 324 forms aerial images on the light sensing element (e.g., CCD array) of the lenslet camera 312 from the returned light reflected by the mirror 322. The waveplate 320 can help to reduce the amount of unwanted backscattered or stray light to improve the signal intensity or the contrast of the aerial images. The lenslet array 324 focuses portions of the light that has initially passed through the optical components of the eye E so that the refractive wavefront aberration effects of the eye E can be determined, similar to what is disclosed in Williams. In this regard, once the wavefront aberrations, and thus phase error, of the eye E have been determined, they can be transformed to a required ablation profile for removal of corneal tissue to correct or improve vision by taking appropriate account of parameters of the eye E (e.g., the refractive indices of eye E components, and/or other parameters). One technique for determining an appropriate profile is to simply scale the wavefront data such that the scaled data generally corresponds to the amount of tissue needed to be removed from the patient's cornea. Laser systems can then remove that profile of tissue from the cornea. Marks on the eye E can be employed to aid in aligning the eye E during acquisition of wavefront sensor data.

Preferably, the lenslet array 324 is an array of approximately 25×25 lenslets, each 600 square microns, such as a 0600-40-S manufactured by Adaptive Optics Associates, Incorporated. This lenslet size is smaller than the lenslet size described in the aforementioned U.S. Pat. No. 5,777,719 and in other systems, and is made possible because of the enhanced intensity of light to the lenslet camera 312 provided by components of the wavefront sensor 300 to be discussed below. The optical path of the wavefront sensor 300 shown in FIG. 12 can also include lenses 326 (e.g., four lenses) and diaphragms or apertures 327 (to allow changes in beam sizes) that are typical of illumination, imaging, and focusing optics, and which also can represent other possible optical components omitted for clarity. For example, in one embodiment of the invention, the focal length of one or both of the lenses 326 about the trombone focusing prism 314 can be changed, perhaps shortened, to accommodate a smaller beam width entering the lenslet array 324. In another embodiment, the range of possible dioptric measurements that can be made with the wavefront sensor 300 (or 102) can be changed, for example, with appropriate selection of the lens 326 in front of the laser 306, to adjust for the natural distribution of poor eyesight in the general or a select population of patients. One way to do this is to position the lens 326 (e.g., a −5 diopter lens) in front of the laser diode 306 such that the laser beam is no longer parallel. This provides a certain offset in diopters that can be used to test the patient's eye with the wavefront sensor 300 (or 102). In a nonlimiting example, the dioptric range can be modified from a symmetrical −8 to +8 diopters with a symmetrical design to an asymmetrical −13 to +3 diopters with an asymmetrical design, as will be appreciated by those skilled in the art. This can be done without changing the size of the trombone focusing prism 314 (or other tuning device) and/or parameters of the optics.

Alternatively to the position of the lens 326, a lens 338 could be moved into the path to the lenslet camera 312. A number of locations within the path to the lenslet camera 312 can be employed to adjust the overall range of the captured wavefront sensor 300. It will be appreciated that by employing either the lens 326 or 338 moveable into and out of position, the length of "throw" necessary for the trombone is reduced. Further, the laser diode 306 typically will have some inherent "astigmatism" of its own. This can be aligned with astigmatism typically found in a patient's eye E, again increasing the overall range of the wavefront sensor 300. Specifically, such astigmatism is aligned "with the rule" as typical patient's astigmatism is found, and the lenslet camera 312 and corresponding wavefront sensor 300 software can take into account this inherent astigmatism as providing an even greater range of determinable astigmatism.

A pupil camera 328 is shown receiving (e.g., 20% of) the reflected light from the beamsplitter 318. The pupil camera 328 preferably provides the iris image data 132 for the iris image 136 via a control system (not shown) similar to or the same as the control system 156 discussed below in the discussion of alignment techniques. To compare, data from the lenslet camera 312 is processed and ultimately provided as the aberration data.

The pupil camera 328 is placed in the optical path between the eye E and the trombone focusing prism 314, which allows the pupil camera 328 to focus on the pupil and iris of the eye E, irrespective of changes in the focal length of the remainder of the system for focusing on the retina. Thus, the pupil camera 328 can develop a clear image of the surface of the eye E independent of the depth of the eye E and the corresponding distance from the retina to the iris.

Fixation Target

The wavefront sensor 300 (and 102) also employs an image used as a fixation target 334, as shown in FIG. 10. The fixation target 334 is illuminated by a light source 336, and allows the patient to fixate and focus while the adjustment camera 323 is focused by the prism 314 on the retina. The fixation target 334 is useful when the aerial images from the lenslet array 324 are brought into focus onto the sensor of the lenslet camera 312 by adjustment of the trombone optics 314. The system advantageously provides an image for the fixation target 334, a nonlimiting example of which is the sailboat on water illustrated in FIG. 10, and not simply a fixation point. The fixation target 334 gives the eye E and the patient's brain a picture-like or actual picture image or scene—really some object or scene being viewed by the eye E—on which to focus. Focusing the eye E with a picture-like image typically is easier to accomplish than focusing to a point. The image of the fixation target allows the eye E to focus at infinity, as if the image were far away, which can aid in eliminating or reducing the effects of eye E accommodation or rotation as the aerial images are focused or the wavefront sensor data are acquired. In other words, the image of the fixation target prevents, or helps prevent to a certain extent, the eye E from focusing at less than infinity.

The fixation target image forces the eye E to rotate to its "normal" rotational position, thus minimizing rotational errors from the diagnostic analysis. Thus, with the fixation target 334, a rotational frame of reference can be defined relative to the eye E. An asymmetrical image, such as the sailboat in FIG. 10, that can be viewed at infinite eye E focus is preferable for helping the eye E maintain the normal or a pre-determined rotational position with respect to the fixation target 334, even with slight head movement. The fixation target 334 can also be used to adjust the rotational position of the eye E in conjunction with recognition, location, and alignment of an iris of the eye E, such as that described above. A similar image can be used in other components according to the present invention, both diagnostic and treatment, to eliminate or reduce accommodation or rotational issues.

It will be appreciated by those skilled in the art having the benefit of this disclosure that various types of components can be used to substitute for components implemented in the wavefront sensor 300 (or 102), and various optical configurations are possible to form other embodiments of the invention. For example, a high intensity, collimated light source, or multiple light sources, for example, one low power and one high power, can replace the laser diode 306. The adjustment camera 323 can instead be placed in the path of the mirror 322, and the lenslet array 324 of the lenslet camera 312 can have more or fewer lenslets, as desired or according to design. Further, it will be appreciated by those skilled in the art that all of these components are generally controlled by a control system, such as a microcomputer. A wide variety of other configurations are possible that are within the scope and spirit of the present invention.

CONCLUSION

The foregoing disclosure and description of the invention are illustrative and explanatory thereof, and various changes in the details of the illustrated apparatus and construction and method of operation may be made without departing from the spirit of the invention.

We claim:

1. A system for aligning a laser refractive correction instrument with a patient's eye comprising:
   a refractive diagnostic tool adapted to provide refractive data about the patient's eye, wherein the refractive diagnostic tool comprises:
   a first camera adapted to acquire a first iris image of the patient's eye, wherein the refractive diagnostic tool is also adapted to spatially relate iris data representing the first iris image to said refractive characteristic data; and
   a laser system adapted to apply a course of refractive treatment to the patient's eye, wherein the laser system comprises:
   a second camera adapted to acquire a second iris image of the patient's eye,
   a laser adapted to apply the course of refractive treatment, and
   a control system for initiating the course of refractive treatment, the control system being adapted to receive data derived from the refractive characteristic data and the spatially related iris data and to align the iris data to the second iris image before the control system initiates the course of refractive treatment.

2. The system of claim 1, wherein the control system is coupled to the second camera and the laser.

3. The system of claim 1, wherein the refractive diagnostic tool comprises a wavefront sensor.

4. The system of claim 1, wherein the refractive diagnostic tool comprises a corneal topography analyzer.

5. The system of claim 1, wherein the refractive diagnostic tool is adapted to determine corneal thickness or other differential profiles using ultrasound.

6. The system of claim 1, wherein the refractive diagnostic tool comprises a hand-held refractive diagnostic tool.

7. The system of claim 1, wherein the laser system further comprises:
   a display coupled to the second camera and the control system, and adapted to display the second iris image and the received iris data overlaid.

8. The system of claim 1, wherein the control system is adapted to compare and to align the received iris data to the second iris image.

9. The system of claim 1, further comprising:
   a second refractive diagnostic tool comprising:
   a third camera adapted to acquire a third iris image, wherein the second refractive diagnostic tool is coupled to the laser system, and adapted to provide additional refractive data for the patient's eye and additional refractive characteristic data and corresponding spatially related additional iris data representing the third iris image from the third camera.

10. The system of claim 9, further comprising:
    a computational system coupled to the refractive diagnostic tool, the second refractive diagnostic tool, and the laser system, wherein the computational system is adapted to receive the refractive characteristic data, the additional refractive characteristic data, the received iris data, and the additional iris data, and is adapted to spatially normalize the refractive characteristic data to the second refractive characteristic data by aligning the received iris data with the additional iris data.

11. The system of claim 10, wherein the computational system is adapted to develop the course of refractive treatment for the laser system based on the normalized data.

12. The system of claim 11, wherein the laser system comprises the computational system.

13. The system of claim 1, wherein the laser comprises an excimer laser.

14. The system of claim 1, further comprising:
    a computational system coupled to the refractive diagnostic tool and the laser system, and adapted to receive the refractive characteristic data and the iris data, to develop the course of refractive treatment, and to provide the course of refractive treatment spatially normalized to the iris data.

15. The system of claim 14, wherein the laser system comprises the computational system.

* * * * *